United States Patent
Liu et al.

(10) Patent No.: US 10,167,490 B2
(45) Date of Patent: Jan. 1, 2019

(54) ERGOTHIONEINE PRODUCTION THROUGH METABOLIC ENGINEERING

(71) Applicants: Pinghua Liu, Newton, MA (US); Heng Song, Allston, MA (US); Wen Hu, Boston, MA (US)

(72) Inventors: Pinghua Liu, Newton, MA (US); Heng Song, Allston, MA (US); Wen Hu, Boston, MA (US)

(73) Assignee: Ergo Health LLC, Newton, MA (US)

( * ) Notice: Subject to any disclaimer, the term of this patent is extended or adjusted under 35 U.S.C. 154(b) by 559 days.

(21) Appl. No.: 14/428,061

(22) PCT Filed: Dec. 20, 2013

(86) PCT No.: PCT/US2013/077287
§ 371 (c)(1),
(2) Date: Mar. 13, 2015

(87) PCT Pub. No.: WO2014/100752
PCT Pub. Date: Jun. 26, 2014

(65) Prior Publication Data
US 2015/0225755 A1 Aug. 13, 2015

Related U.S. Application Data

(60) Provisional application No. 61/740,829, filed on Dec. 21, 2012.

(51) Int. Cl.
| | |
|---|---|
| *C12P 17/10* | (2006.01) |
| *C12N 15/52* | (2006.01) |
| *C12P 13/04* | (2006.01) |
| *C07D 233/42* | (2006.01) |

(52) U.S. Cl.
CPC ............ *C12P 17/10* (2013.01); *C07D 233/42* (2013.01); *C12N 15/52* (2013.01); *C12P 13/04* (2013.01)

(58) Field of Classification Search
CPC .......... C12P 17/10; C12P 13/04; C12N 15/52; C07D 233/42
See application file for complete search history.

(56) References Cited

U.S. PATENT DOCUMENTS

| | | | |
|---|---|---|---|
| 4,980,285 A | 12/1990 | Sano et al. | |
| 5,631,150 A | 5/1997 | Harkki et al. | |
| 5,707,828 A | 1/1998 | Sreekrishna et al. | |
| 5,759,828 A | 6/1998 | Tal et al. | |
| 5,888,783 A | 3/1999 | Tomita et al. | |
| 5,919,670 A | 7/1999 | Okamoto et al. | |
| 2006/0269988 A1* | 11/2006 | Royer | C07K 14/195 435/69.1 |
| 2008/0193373 A1* | 8/2008 | Stritzker | A61K 33/24 424/1.17 |
| 2012/0136159 A1 | 5/2012 | Erdelmeier | |

OTHER PUBLICATIONS

Kizer L et al. Application of Functional Genomics to Pathway Optimization for Increased Isoprenoid Production. 2008. Applied and Environmental Microbiology. vol. 74, No. 10. p. 3229-3241.*
Prather KLJ et al. De novo biosynthetic pathways: rational design of microbial chemical factories. 2008. Current Opinion in Biotechnology. 19:468-474.*
Park J et al. Enzymatic synthesis of S-adenosyl-L-methionine on the Preparative Scale. 1996. Bioorganic & Medicinal Chemistry. vol. 4, No. 12. p. 2179-2185.*
Baldwin et al. "Isopenicillin N Synthase: Mechanistic Studies." *Chem. Rev.* 90.7(1990):1079-1088.
Bello et al. "The *Neurospora crassa* Mutant NcΔEgt-1 Identifies an Ergothioneine Biosynthetic Gene and Demonstrates that Ergothioneine Enhances Conidial Survival and Protects Against Peroxide Toxicity During Conidial Germination." *Fungal Genet. Biol.* 49.2(201):160-172.
Branshausen et al. "Identification and Characterization of the First Ovothiol Biosynthetic Enzyme." *J. Am. Chem. Soc.* 133.6(2011):1757-1759.
Briggs. "Ergothioneine in the Central Nervous System." *J. Neurochem.* 19.1(1972):27-35.
Chiang et al. "S-Adenosylmethionine and Methylation." *FASEB J.* 10.4(1996):471-480.
Epand et al. "Study of the Ergothioneine Concentration in the Blood of Individuals with Diabetes Mellitus." *J. Clin. Chem. Clin. Biochem.* 26.10(1988):623-626.
Erdelmeier et al. "Cysteine as a Sustainable Sulfur Reagent for the Protecting-Group-Free Synthesis of Sulfur-Containing Amino Acids: Biomimetic Synthesis of L-ergothioneine in Water." *Green Chem.* 14(2012):2256-2265.
Fahey et al. "Analysis of Biological Thiols: Quantitative Determination of Thiols at the Picomole Level Based upon Derivation with Monobromobimanes and Separation by Cation-Exchange Chromatography." *Anal. Biochem.* 111.2(1981):357-365.
Fahey. "Novel Thiols of Prokaryotes." *Ann. Rev. Microbiol.* 55(2001):333-356.
Genghof et al. "Biosynthesis of Ergothioneine from Endogenous Hercynine in *Mycobacterium smegmatis*." *J. Bacteriol.* 95.2(1968):340-344.
Gründemann et al. "Discovery of the Ergothioneine Transporter." *PNAS.* 102.14(2005):5256-5261.
Hand et al. "Biological Chemistry of Naturally Occurring Thiols of Microbial and Marine Origin." *J. Natural Prod.* 68.2(2005):293-308.
Hartman. "Ergothioneine as Antioxidant." *Meth. Enzymol.* 186(1990):310-318.

(Continued)

*Primary Examiner* — Paul J Holland
(74) *Attorney, Agent, or Firm* — Fox Rothschild LLP

(57) ABSTRACT

The present disclosure relates to the production of ergothioneine through either in vitro enzymatic transformations or fermentations using microbials created by metabolic engineering. Also disclosed are transformed cells useful in such methods and ergothioneine produced by such methods. Transformed cells of the disclosure are capable of converting histidine and cysteine or hercynine and cysteine into ergothioneine in greater efficiency than the untransformed wild-type cells.

9 Claims, 7 Drawing Sheets

Specification includes a Sequence Listing.

(56) References Cited

OTHER PUBLICATIONS

Melville et al. "Ergothioneine in Microorganisms." *J. Biol. Chem.* 223.1(1956):9-17.
Melville et al. "The Occurence of Ergothioneine in Plant Material." *J. Biol. Chem.* 218.2(1956):647-651.
Paul et al. "The Unusual Amino Acid L-Ergothioneine is a Physiologic Cytoprotectant." *Cell Death Differentiation.* 17.7(2010):1134-1140.
Scott et al. "Purification and Properties of Glutathione Reductase of Human Erythrocytes." *J. Biol. Chem.* 238(1963):3928-3933.
Seebeck. "In Vitro Reconstitution of Mycobacterial Ergothioneine Biosynthesis." *J. Am. Chem. Soc.* 132.19(2010):6632-6633.
Tanret. "Chimie Organique." *Comptes rendus de l'Academie des Sciences.* 149(1909):222-224. (French original and English translation).
Weaver et al. "Thiol/Disulfide Exchange—Reactions of Ovothiol A with Glutathione." *J. Org. Chem.* 60.6(1995):1904-1907.
Xu et al. "Synthesis of L-(+)-Ergothioneine." *J. Org. Chem.* 60.20(1995):6296-6301.

\* cited by examiner

A. Proposed ergothioneine biosynthetic pathway.

B. Proposed ovothiol biosynthetic pathway.

Figure 1. Proposed biosynthetic pathways for ergothioneine and ovothiol.

A. Pathway A.

A. Pathway B.

I. Oxygen consumption assay.

II. ¹H-NMR assay by monitoring the chemical shift of the imidazole protons.

Figure 3. Two different assays for EgtB and OvoA catalysis.

Figure 4. Ergothioneine biosynthetic enzymes. A) Purified ergothioneine biosynthetic enyzmes; B) UV-visible spectrum of purififed EgtE protein. These enzymes can be easily produced and purified at hundres of mg scales. The UV-visible spectrum of the purified EgtE is consistent with the presence of a PLP cofactor.

Figure 5. New OvoA chemistries (2 to 4 conversion).

Figure 6. Construct (Ego-1) for the production of ergothioneine in *E. coli*.

Figure 7. Construct (Ego-2) to further enhance ergothioneine production.

ERGOTHIONEINE PRODUCTION THROUGH METABOLIC ENGINEERING

RELATED APPLICATIONS

This application is a national stage application, filed under 35 U.S.C. § 371, of International Application No. PCT/US2013/077287, filed on Dec. 20, 2013, which claims priority to U.S. Provisional Application No. 61/740829 filed Dec 20, 2012, the contents of which are hereby incorporated by reference in its entirety.

GOVERNMENT SUPPORT

This invention was made with government support under grant no. GM093903 awarded by the National Institutes of Health and no. CHE-0748504 awarded by the National Science Foundation. The government has certain rights in the invention.

TECHNICAL FIELD

The present disclosure relates generally to production of ergothioneine through either cell-free enzymatic transformations or fermentation using strains created by metabolic engineering.

BACKGROUND

Ergothioneine is a thiol-containing amino acid isolated from ergot by Tanret in 1909. Its unique redox-properties makes it one of the best natural anti-oxidants. In addition, due to its specific enrichment from the food by many human tissues (e.g., liver, kidney, central nervous system and red blood cells), ergothioneine was proposed to have many beneficial role in human physiology. Currently, ergothioneine is widely used as the key component in anti-ageing products with a market of billions of dollars.

Ergothioneine is produced from two amino acids (histidine and cysteine) through five-enzymatic steps. However there are three major barriers preventing the utilization of the currently known ergothionine biosynthetic pathway for its production through fermentation: (i) the EgtE enzyme cannot be overexpressed; (ii) the activity of EgtB is low; 3) the potential competition between ergothioneine and glutathione for γ-Glu-Cys, which will limit the production yield. Accordingly, currently, ergothioneine is produced using chemical approaches. As such, there remains a need in the art for recombinant biosynthesis of ergothioneine.

SUMMARY

Provided herein are a novel enzymatic method and a metabolic engineering method for increasing, enhancing, or maximizing production of ergothioneine in either a cell-free enzymatic system or a cell culture system. The cell-free enzymatic system and the cellculture system using engineered microbials created by metabolic engineering disclosed herein can be used to produce ergothioneine at higher levels. These processes described herein are based on inventors' discoveries: 1) Successful production of EgtE in *E. coli* and identification of conditions to improve EgtB activities, which enables the production of ergothioneine using the currently known ergothioneine biosynthetic pathway by either cell-free transformations or by fermentations. 2) An enzyme from the ovothiol biosynthetic pathway (OvoA) can be used to catalyze the direct oxidative coupling of Cys and trimethyl-histidine to produce a key intermediate needed in the biosynthesis of ergothioneine. Such a discovery is surprising and unexpected because OvoA also catalyzes the oxidative coupling of Cys and His to produce a structurally completely different compound. Without wishing to be bound by a theory, the newly discovered OvoA activity can shorten the ergothioneine biosynthetic pathway by two steps and can eliminate the competition between ergothioneine and glutathioneine biosynthesis. Ergothioneine can be produced by either cell-free enzymatic system or cell culture system based on the newly discovered OvoA chemistry. 3) Another enzyme NcEgt1 was also able to catalyze the direct coupling between Cys and trimethyl-histidine. Ergothioneine can be produced by either cell-free enzymatic system or cell culture system based on the newly discovered NcEgt1 chemistry.

Accordingly, certain aspects provided herein relate to in vitro cell-free system comprising recombinantly expressed one or more genes of the ergothioneine biosynthetic pathway and one or more genes of the ovothiol biosynthetic pathway or their homologs identified through bioinformatics approach (e.g., NcEgt1). The other aspect involves microbial strains created through metabolic engineering using these enzymes to produce ergothioneine through fermentation.

In some embodiments, the cell recombinantly expresses: (i) a egtA gene; (ii) a egtB gene; (iii) a egtC gene; (iv) a egtD; and (iv) a egtE gene and a gene encoding FAD synthetase. In some embodiments, the cell further expresses a gene encoding a SAM synthetase.

In some embodiments, the cell recombinantly expresses: (i) a ovoA gene or a ncEgt-1 gene or their homologs identified by bioinformatics; and (ii) a egtE gene and a gene encoding FAD synthetase.

In some embodiments, the cell recombinantly expresses: (i) a egtD gene; (ii) a ovoA gene or a ncEgt-1 gene; and (iii) a egtE gene and a gene encoding FAD synthetase. In some embodiments, the cell recombinantly express: (i) a egtD gene; (ii) a ovoA gene or a ncEgt-1 gene; and (iii) a egtE gene and a gene encoding FAD synthetase; and (iv) a gene encoding a SAM synthetase.

Some aspects provided herein are directed to cell culture medium, cell-free enzymatic mixture, or supernatant after lysing cells collected from fermentations of any of the aspects or embodiments described herein.

Other aspects provided herein are directed to a method, comprising culturing in cell culture medium of any one of the aspects or embodiments described herein.

Still other aspects provided herein are directed to a method comprising incubating a cell extract obtained from lysis of the cell(s) described herein.

Various aspects described herein related to a method, which comprises recombinantly expressing in a cell one or more genes of the ergothioneine biosynthetic pathway and one or more genes of the ovothiol biosynthetic pathway or other homologs identified by bioinformatics (e.g., NcEgt1).

Some aspects provided herein are directed to a method for preparing ergothioneine.

In some embodiments, the method comprises recombinantly expressing in a cell: (i) EgtA protein or a functional fragment thereof retaining enzymatic activity; (ii) EgtB protein or a functional fragment thereof retaining enzymatic activity; (iii) EgtC protein or a functional fragment thereof retaining enzymatic activity; (iv) EgtD protein or a functional fragment thereof retaining enzymatic activity; (v) EgtE protein or a functional fragment thereof retaining enzymatic activity; and (vi) a gene encoding FAD synthetase or a functional fragment thereof retaining enzymatic activity.

In some embodiments, the method comprises recombinantly expressing in a cell: (i) a ovoA or a ncEgt-1 gene or other homologs identified by bioinformatics; and (ii) a egtE gene and a gene encoding FAD synthetase.

In some embodiments, the method comprises recombinantly expressing in a cell: (i) a egtD gene; (ii) a ovoA gene or ncEgt-1 gene or other homologs identified by bioinformatics; and (iii) a egtE gene and a gene encoding FAD synthetase.

In some embodiments, the method described herein further comprises culturing in cell culture medium the cell described herein.

In some embodiments, the method described herein comprises culturing in cell culture medium the cell described herein, wherein the culture medium is supplemented with cysteine, histidine or hercynine.

In some embodiments, the cell culture medium is further supplemented with one or more iron salts.

In some embodiments, the method described herein further comprises collecting cell culture medium or supernatant after lysing the cells described herein.

In some embodiments, the method described herein further comprises recovering ergothioneine from the cell or from the culture medium in which the cell is grown.

BRIEF DESCRIPTION OF THE DRAWINGS

FIG. 9A, partially purified ergothioneine; FIG. 9B, after adding pure ergothioneine to confirm the identity of the product generated from fermentation.

DETAILED DESCRIPTION

Figure 1:
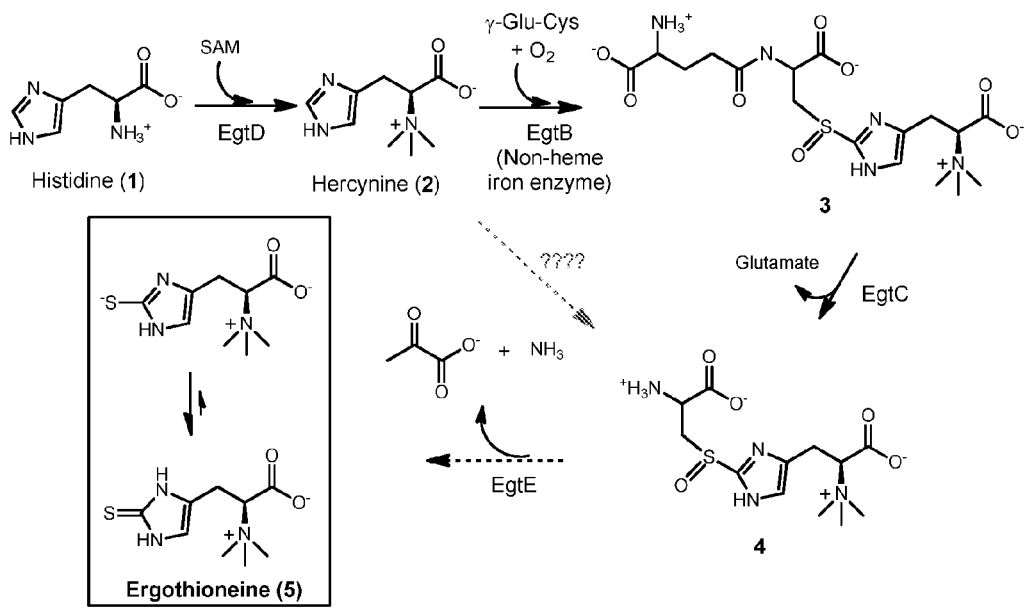
FIG. 1 is a schematic representation of the proposed biosynthetic pathways for ergothioneine and ovothiol.
Figure 1:
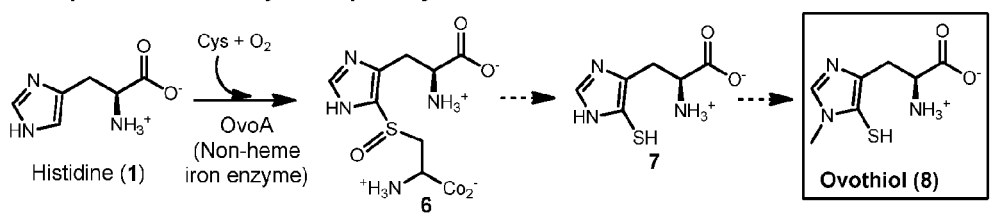

To the extent that genes, other nucleic acid sequences, and amino acid sequences from a particular microorganism are discussed and/or exemplified below, it will be appreciated that other microorganisms have similar metabolic pathways, as well as genes and proteins having similar structure and function within such pathways. As such, the principles discussed below with regard to any particular microorganism, either as a source of genetic material or a host cell to be modified, are applicable to other microorganisms and are expressly encompassed by the present invention.

In part, this invention is based on the inventors' discovery that the enzyme OvoA from the ovothiol biosynthetic pathway can be used to produce an intermediate in the ergothioneine biosynthesis. The inventors have discovered, inter alia, that the enzyme OvoA (or NcEgt1) can catalyze the oxidative coupling between hercynine and cysteine to produce the compound

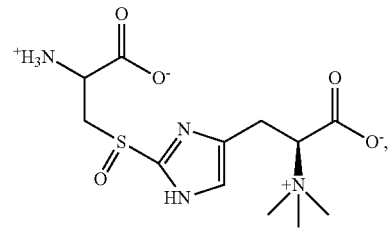

which is an intermediate in the biosynthesis of ergothioneine. This is surprising and unexpected since the OvoA usually catalyzes coupling of histidine and cysteine to produce the compound

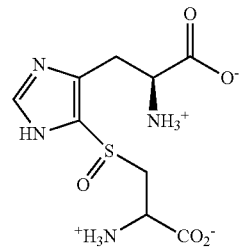

As can be seen, the location where the cysteine links on the imidazole ring is different between the two products: an unexpected and surprising result.

In part, a separate part of this invention is based on the production of EgtE, whose expression has not been feasible previously. The inventors have discovered inter alia that EgtE can be recombinantly produced under a genetic background that has a FAD synthetase.

Accordingly, disclosed herein are cells that recombinantly express one or more genes described herein, and the use of such cells in producing ergothioneine. The cell can recombinantly express one or more genes of the ergothioneine biosynthetic pathway and one or more genes of the ovothiol biosynthetic pathway.

In some embodiments, the cell is transformed to recombinantly express at least one of: (i) EgtA protein or a functional fragment thereof retaining enzymatic activity; (ii) EgtB protein or a functional fragment thereof retaining enzymatic activity; (iii) EgtC protein or a functional fragment thereof retaining enzymatic activity; (iv) EgtD protein or a functional fragment thereof retaining enzymatic activity; and (v) EgtE protein or a functional fragment thereof retaining enzymatic activity and a gene encoding FAD synthetase or a functional fragment thereof retaining enzymatic activity.

In some embodiments, the cell is further transformed to recombinantly express a SAM synthetase or a functional fragment thereof retaining enzymatic activity.

In some embodiments, the cell is transformed to recombinantly express at least one of: (i) a ovoA or a ncEgt-1 gene; and (ii) a egtE gene and a gene encoding FAD synthetase.

In some other embodiments, the cell is transformed to recombinantly express at least an egtD gene in addition to one of (i) a ovoA gene or a ncEgt-1 gene; and (ii) a egtE gene and a gene encoding FAD synthetase. In some further embodiments of this, the cell is still further transformed to recombinantly express a gene encoding a SAM synthetase.

In some embodiments, the cell recombinantly expresses: (i) a ovoA or a ncEgt-1 gene; and (ii) a egtE gene and a gene encoding FAD synthetase.

In some other embodiments, the cell recombinantly expresses: (i) a ovoA or a ncEgt-1 gene; (ii) a egtE gene; and (iii) a gene encoding an FAD synthetase.

In some embodiments, the cell recombinantly expresses: (i) a egtD gene; (ii) a ovoA gene or a ncEgt-1 gene; and (iii) a egtE gene and a gene encoding FAD synthetase.

In some other embodiments, the cell recombinantly expresses: (i) a egtD gene; (ii) a ovoA gene or a ncEgt-1 gene; (iii) a egtE gene and a gene encoding FAD synthetase; and (iv) a gene encoding a SAM synthetase.

In still some other embodiments, the cell recombinantly expresses: (i) a egtD gene; (ii) a ovoA gene or a ncEgt-1 gene; (iii) a egtE gene and a gene encoding FAD synthetase; (iv) a gene encoding a SAM synthetase.

In any of the aspects or embodiments described herein, the cell can endogenously express one or more of: (i) a egtD gene; (ii) a ovoA gene or a ncEgt-1 gene; (iii) a egtE gene and a gene encoding FAD synthetase; (iv) a gene encoding a SAM synthetase.

In some embodiments, the transformed cell described herein recombinantly expresses a codon optimized gene. For example, the cell recombinantly expresses at codon optimized egtD gene, ovoA gene, ncEgt-1 gene, egtE gene, the gene encoding a SAM synthetase, or a gene encoding FAD synthetase.

As used herein, the term "cell", "host cell" or "cell line" is intended to refer to well-characterized homogenous, biologically pure populations of cells. These cells can be eukaryotic cells that are neoplastic or which have been "immortalized" in vitro by methods known in the art, as well as primary cells, or prokaryotic cells. Without limitation, the host cell or the cell line can be of mammalian, plant, insect, fungal (including yeast), or bacterial origin.

In some embodiments, the cell is a bacterial cell. In some further embodiments of this, the cell is *E. coli* or *S. pyogenes*. Exemplary strains of *E. coli* amenable to various aspects described herein include, but are not limited to, BL21 (DE3), BL21 (DE3) pLysS, BL21 (DE3)pLysE, BL21 (DE3)pLacI, BL21trxB(DE3), BL21trxB(DE3)pLysS, BLR (DE3), BLR(DE3)pLysS, AD494(DE3), AD494(DE3)pLysS, HMS174(DE3), HMS174(DE3)pLysS, HMS174(DE3) pLysE, Origami(DE3), Origami(DE3)pLysS, Origami(DE3) pLysE, Origami(DE3)pLacI , OrigamiB(DE3), OrigamiB (DE3)pLysS, OrigamiB(DE3)pLysE, OrigamiB(DE3)pLacI, Rosetta(DE3), Rosetta(DE3)pLysS, Rosetta(DE3)pLysE, Rosetta(DE3)pLacI, Tuner(DE3), Tuner(DE3)pLysS and Tuner(DE3)pLacI.

In some other embodiments, the cell can be from an insect (e.g., Sf9, high five and Sf21 cell), yeast (e.g., *P. pastoris, P. methanolica, S. pombe* and *S. cerevisiae*), mammalian (e.g., Chinese hamster ovary cells (CHO), Cos-1, CV-1, HeLa, NIH3T3, PER-C6 and NSO) or a plant. Other suitable cells are also known to those skilled in the art.

As used herein, the term "transfected" or "transformed" includes any cell, host cell or cell line the genome of which has been altered or augmented by the presence of at least one polynucleotide, e.g., DNA sequence, which is also referred to in the art of genetic engineering as "heterologous DNA," "recombinant DNA," "exogenous DNA," "genetically engineered," "non-native," or "foreign DNA," wherein said DNA was isolated and introduced into the host cell or cell line by the process of genetic manipulation. The transfected DNA can be maintained as an extrachromosomal element or as an element which is stably integrated into the host chromosome of the host cell. Host cells with transfected DNA maintained as an extrachromosomal element or as an element stable integrated into the host chromosome are referred to as a "recombinant host cell" or "transformed cell" herein.

It should be appreciated that some cells compatible with the invention can express an endogenous copy of one or more of the genes described herein as well as a recombinant copy thereof. In some embodiments if a cell has an endogenous copy of one or more of the genes described herein then then the cells and methods described herein will not necessarily require adding a recombinant copy of the gene(s) that are endogenously expressed. In some embodiments the cell can endogenously express one or more enzymes from the pathways described herein and can recombinantly express one or more other enzymes from the pathways described herein for efficient production of ergothioneine.

In some embodiments, the untransformed cell, e.g., a wild-type cell doesn't produce ergothioneine.

In some embodiments, the transformed cell can produce ergothioneine in an amount that is at least (e.g. at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 1.25-fold, at least 1.5-fold, at least 2-fold, at least 5-fold, at least 10-fold, at least 25-fold, at least 50-fold, at least 75-fold, at least 100-fold or higher) relative to amount of ergothioneine produced by a untransformed host cell under same conditions.

The polypeptide encoded by the ovoA gene (OvoA enzyme) is a 5-histidylcysteine sulfoxide synthase. OvoA is a mononuclear non-heme enzyme and catalyzes a four-electron oxidation process. OvoA was the first ovothiol biosynthetic enzyme as characterized from *Erwinia tasmaniensis* and *Trypanosoma cruzi*. Homologous Enzymes homologues OvoA are encoded in more than 80 genomes ranging from proteobacteria to fungi.

The polypeptide encoded by the ncEgt-1 gene (NcEgt-1 enzyme from *Neurospora crassa*) catalyzes the formation of

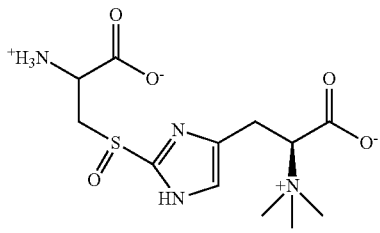

from hercynine and cysteine.

The polypeptide encoded by the egtE gene (EgtE enzyme) catalyzes the cleavage of a C—S bond in the product of oxidative coupling between hercynine and cysteine.

The polypeptide encoded by the egtD gene (EgtD enzyme) enzyme catalyzes the N-methylation of histidine to produce hercynine.

As EgtD is a SAM dependent methyltransferase, a SAM synthetase can be co-expressed with EgtD to enhance activity of EgtD. Accordingly, in some embodiments, the cell can be further transformed to recombinantly express a gene encoding a SAM synthetase. The enzyme SAM synthetase (EC 2.5.1.6) catalyzes the conversion of methionine and ATP into S-denosylmethionine (AdoMet or SAM). The genes for SAM synthetase, which catalyzes the conversion of methionine to SAM, have been cloned from *E. coli*.

Since SAM synthetase substrates are methionine and ATP, the cell culture media, for production of ergothioneine, can be further supplemented with methionine in addition to histidine or hercynine.

The inventors have discovered that expression of EgtE in a cell can be enhanced under a condition that has FAD synthetase. FAD synthetase catalyzes the formation of flavin adenine dinucleotide from riboflavin and ATP.

Thus, in some embodiments, the cell can be further transformed to recombinantly express a gene encoding a FAD synthetase or a functional fragment thereof retaining enzymatic activity.

Since, the uptake and maturation of the metallo-enzymes (EgtB or OvoA) is essential for maximum efficacy, a Fe uptake system can be included in the transformed cells for producing ergothioneine. For example, the host cell can be further transformed to express a siderophore, e.g., a polynucleotide encoding a siderophore or functional fragment thereof and supplementing the medium with one or more iron salts.

It would be appreciated by one of skill in the art that the genes described herein can be obtained from a variety of sources.

In some embodiments, the ovoA gene is an oxidase and comprises the nucleotide sequence of SEQ ID NO: 1 (ETA_00030 [*Erwinia tasmaniensis* Et1/99], ACCESSION YP_001905965:

ATGGCAAAATGGGAGCACGACGTGACCGCGCAACAACACCAGACAGGATT

ACCCGCCCCAACCCGCATGCTGACGCTCAGCGGTGGCGATCCACAACAAA

AACGACTGCAGATACTGAGCGACTTCAGCAAGACCTGGGAACTCTATGAA

AGCCTGTTTGACTGCCTTACCGATGAGCGCGCCTGGTACACCAAGGCCAT

TTCACTGCGTCACCCGCTGATCTTCTATTACGGCCATACCGCCACCTTCT

ATATCAACAAGTTGATGGCGGGGGGGCTTATCGACGCGCGCGTTGACGAC

AGGATCGAAGCGACAATGGCGATTGGCGTCGACGAAATGAGCTGGGACGA

CCTGGATAACAGCCACTACAGCTGGCCGTCGCTGGCAGAACTGCGCGACT

ATCGTGGAAAAGTTCGCCACCTCGTTGAGCAGTTTATTCAGCAGATGCCG

TTGACGTTGCCGATCGGCTGGGATAGCCCGGCATGGGTTATCCTGATGGG

GATCGAGCATGAGCGCATCCATCTGGAAACCTCAAGCGTGCTGATCCGCC

AGCTGCCGCTGGCGTGGGTCAGCGCCCAGCCGCACTGGCCTGCCTGTCCC

GATGCGCGTCACGATCGTATGGCGGTGCCGGCCAACAGCCTGGTACAGGT

CGCCGGTCGCCGCGTGACGCAGGGGAAAACGGATGATACCTACGGCTGGG

ATAATGAGTACGGCAGCCTGGTCACCGAAGTGAAGCCATTTCAGGCCAGC

CGCATGCTGGTCAGTCATGCCGAATTTTTTGCTTTCGTTGCCGCGGGAGG

CTATCAGAACCAACGCTGGTGGGATGACGAAGGCTGGGCTGGCGTGAAT

TTTCCGCGGCGGAGATGCCGACCTTTTGGCGAGGTTCACCACAGCAGCCG

GAAGAATTAAGGCTGCGCCTGCTGGCAGAAGAAGTGGCGATGCCGTGGGA

CTGGCCGGCCGAGGTCAATCAGCTGGAGGCTGCCGCATTCTGCCGCTGGA

AAGCGGAGGAGACCGGCCTGTCGATCCAGCTGCCGGCGGAGAGTGAATGG

ATGAGCCTGCGCGAGCAGGTTGAGGGCGACCAGCCGGACTGGAATGATGC

ACCGGGCAATATTAATCTGGCCTGCTGGGCATCTTCTTGCCCAATAGACC

GCTTTGCCCAGGGCGAATTCTTCGACCTGGTTGGCAATGTCTGGCAGTGG

ACCACGACGCCAATCAACGGTTTTCCGGGCTTTCGCGTCCACCCTTTATA

CGATGATTTCTCCACCCCGACCTTTGATGGCAAACACACGCTGATTAAGG

GCGGCAGCTGGATATCTACCGGCAATGAGGCCCTGAAATCTGCTCGCTAT

GCCTTCCGACGCCATTTCTTCCAGCATGCGGGATTCCGCTATGTGGTTTC

GCAACATCAGGAGAGCCTGCACTCCAACCCGTATGAAACGGACAGCATGG

TGTCACAGTATCTCGATTTCCAGTACGGCCCAGAGTACTTCGCCGTGGAA

AATTACGCCAAGGCGCTGGCGAAGATCGCCTGCGGTATCAGTCAGCACCA

CCAGCGCGCGCTGGATATCGGCTGTGCTACCGGACGTGCCAGCTTTGAGC

TGGCGCGTCATTTTGAGCAGGTGGTCGGAATGGACTACTCGGCGCGTTTT

ATCGACGTGGCTCTGCAACTGACCCGCGGCGAAGATTTCCGCTATGTCAC

CCAGGAAGAAGGCGACCTGGTCGAATACCGTCAGGTGCATTTGCCGGACT

TCGATCTCGGCCCGGAGCAGGCCAGCCGCATCCGGTTTGTACAGGGGGAT

GCCTGCAACCTGAAACCCCAGCAGGAAGCCTGGGATCTGGTGCTGGCCGC

TAACCTGATTGACCGCCTGCGCCAGCCGGCGCGCTTCCTTGCGGACATCG

CGCCCATGATCCGCCCCGGCGGCGTACTGATGCTCTCATCCCCCTATACT

TGGCTTGAAGAGTTCACGCCGAAAGAGAACTGGCTGGGCGGCATTCGTGA

AAACGGCGAAGCGCTCTCGACTTATCAGGCGCTGCAACGTCTGCTGGCCG

CCGACTTTGAGGAGCTGGCCCCGCCTCAGGACGTGCCGTTTGTCATTCGT

GAAACGGCGCGCAAATATCAGCACAGCGTGGCGCAGTTAACCCTGTGGCG

TAAACGTTAG).

In some embodiments, the ncEgt-1 gene is an oxidase and comprises the nucleotide sequence of SEQ ID NO: 2 (*Neurospora crassa* OR74A hypothetical protein NCU04343 partial mRNA, ACCESSION XM_951231, VERSION XM_951231.2 GI:164429491:

ATGCCGAGTGCCGAATCCATGACCCCAAGCAGTGCCCTCGGACAGCTCAA

AGCAACTGGACAACATGTGCTATCCAAGCTTCAGCAGCAGACATCAAACG

CCGATATCATCGACATCCGCCGCGTTGCTGTAGAGATCAACCTCAAGACC

GAGATAACCTCCATGTTCCGACCTAAAGATGGCCCTAGACAGCTACCCAC

CTTGCTTCTCTACAACGAGAGAGGCCTGCAGCTGTTCGAGCGTATCACAT

ACCTTGAAGAGTACTATCTTACCAATGACGAGATCAAAATCCTCACCAAA

CATGCGACCGAAATGGCTAGCTTCATCCCGTCAGGTGCCATGATCATTGA

GCTCGGAAGCGGAAATCTGCGCAAAGTAAACCTTCTATTGGAAGCCCTAG

ACAACGCCGGCAAGGCAATTGACTATTATGCCCTTGACCTGTCTCGGGAG

GAGCTGGAGCGCACTCTCGCTCAGGTACCATCCTACAAGCACGTCAAGTG

CCACGGTCTTCTGGGTACATATGACGATGGACGTGACTGGCTCAAGGCCC

CAGAGAACATCAATAAACAGAAATGCATCTTGCACCTCGGGTCAAGCATT

GACAAGGTTGGTATTACTCACGAGTTCATCTTGAATGGTCTTCGCAACGC

CAATGAAATTATCGGAGAGACGGCCTTCATCGAGGGCGATTGGAGAGTCA

TTGGCGAATATGTGTATGACGAAGAGGGCGGCAGACACCAGGCCTTTTAC

GCCCCCACTCGCGACACCATGGTTATGGGGAGTTGATTAGGTCACACGA

CAGGATCCAGATCGAACAGAGCCTAAAGTACTCGAAAGAGGAGTCAGAGA

GGCTCTGGAGCACGGCGGGATTGGAACAAGTCTCGGAATGGACGTACGGC

AACGAATATGGACTCCATCTGCTTGCCAAGTCAAGGATGTCTTTCAGTCT

CATCCCTTCGGTGTACGCTCGCAGCGCACTCCCAACTCTGGACGACTGGG

AGGCCCTTTGGGCGACATGGGATGTCGTCACACGTCAGATGCTTCCCCAG

GAAGAGCTTCTGGAGAAGCCCATCAAGCTCCGAAACGCCTGCATCTTTTA

CCTCGGTCACATCCCGACCTTCCTCGACATCCAGCTCACAAAGACCACCA

AGCAGGCTCCGTCAGAGCCCGCTCACTTTTGCAAGATCTTCGAGCGAGGC

ATTGATCCTGATGTCGACAACCCGGAGCTGTGTCATGCGCACTCGGAGAT

TCCTGATGAATGGCCGCCGGTGGAAGAAATCCTGACCTACCAGGAGACGG

TACGGTCCCGGTTACGCGGCCTCTATGCGCATGGCATCGCGAATATTCCG

CGGAATGTGGGTCGGGCCATTTGGGTTGGGTTTGAGCACGAGCTTATGCA

TATCGAGACGCTGTTGTACATGATGCTACAGAGCGACAAGACGCTGATCC

CAACCCATATTCCACGGCCCGACTTTGACAAGCTCGCGAGGAAGGCAGAG

TCCGAGAGGGTTCCCAATCAGTGGTTTAAGATTCCGGCACAGGAGATCAC

CATCGGTTTGGATGATCCTGAGGATGGATCTGATATCAACAAGCATTATG

GCTGGGACAACGAGAAGCCTCCAAGGCGCGTTCAAGTTGCTGCCTTTCAG

GCTCAAGGGAGGCCGATCACCAACGAAGAGTACGCGCAATATCTGCTTGA

AAAGAACATCGACAAGCTCCCTGCCTCTTGGGCCCGCCTGGACAACGAGA

ACATTAGCAATGGAACAACAAACAGCGTGAGCGGTCACCACAGCAACAGA

ACCTCCAAGCAGCAGCTCCCTTCATCTTTCCTCGAGAAGACAGCAGTCCG

CACAGTCTACGGTCTCGTGCCTCTCAAGCACGCTCTCGACTGGCCCGTGT

TTGCCTCTTACGACGAACTTGCCGGTTGCGCAGCTTACATGGGCGGCCGT

ATTCCCACCTTCGAAGAGACCCGGAGCATTTACGCTTACGCCGATGCTCT

CAAGAAGAAGAAGGAAGCTGAGAGACAATTGGGAAGGACGGTTCCGGCTG

TTAATGCCCACCTAACCAACAACGGCGTGGAAATCACTCCCCCATCCTCT

CCCTCTTCCGAGACCCCCGCCGAGTCTTCCTCCCCCTCCGACAGCAACAC

CACCCTCATCACCACCGAAGACCTCTTCTCTGACCTAGACGGTGCCAATG

TCGGTTTTCACAACTGGCACCCTATGCCCATCACCTCCAAAGGCAACACC

CTTGTCGGGCAAGGCGAGCTCGGCGGCGTGTGGGAATGGACTTCATCGGT

CCTCCGCAAGTGGGAGGGGTTCGAGCCGATGGAGCTGTACCCCGGCTATA

CGGCGGATTTTTTCGATGAGAAGCACAACATTGTGCTGGGAGGGAGCTGG

GCTACGCATCCGAGGATTGCGGGGAGGAAGAGCTTTGTGAATTGGTACCA

GAGGAATTATCCTTATGCTTGGGTGGGGGCGAGAGTTGTTAGGGATTTGT

GA)

In some embodiments, the egtD gene is a methyltransferase and comprises the nucleotide sequence of SEQ ID NO: 3 (hypothetical protein MSMEG_6247 [*Mycobacterium smegmatis* str. MC2 155], ACCESSION YP_890466, VERSION YP_890466.1 GI:118473274:

ATGACGCTCTCACTGGCCAACTACCTGGCAGCCGACTCGGCCGCCGAAGC

ACTGCGCCGTGACGTCCGCGCGGGCCTCACCGCGGCACCGAAGAGTCTGC

CGCCCAAGTGGTTCTACGACGCCGTCGGCAGTGATCTGTTCGACCAGATC

ACCCGGCTCCCCGAGTATTACCCCACCCGCACCGAGGCGCAGATCCTGCG

GACCCGGTCGGCGGAGATCATCGCGGCCGCGGGTGCCGACACCCTGGTGG

AACTGGGCAGTGGTACGTCGGAGAAAACCCGCATGCTGCTCGACGCCATG

CGCGACGCCGAGTTGCTGCGCCGCTTCATCCCGTTCGACGTCGACGCGGG

CGTGCTGCGCTCGGCCGGGGCGGCAATCGGCGCGGAGTACCCCGGTATCG

AGATCGACGCGGTATGTGGCGATTTCGAGGAACATCTGGGCAAGATCCCG

CATGTCGGACGGCGGCTCGTGGTGTTCCTGGGGTCGACCATCGGCAACCT

GACACCCGCGCCCCGCGCGGAGTTCCTCAGTACTCTCGCGGACACGCTGC

AGCCGGGCGACAGCCTGCTGCTGGGCACCGATCTGGTGAAGGACACCGGC

CGGTTGGTGCGCGCGTACGACGACGCGGCCGGCGTCACCGCGGCGTTCAA

CCGCAACGTGCTGGCCGTGGTGAACCGCGAACTGTCCGCCGATTTCGACC

TCGACGCGTTCGAGCATGTCGCGAAGTGGAACTCCGACGAGGAACGCATC

GAGATGTGGTTGCGTGCCCGCACCGCACAGCATGTCCGCGTCGCGGCACT

GGACCTGGAGGTCGACTTCGCCGCGGGTGAGGAGATGCTCACCGAGGTGT

CCTGCAAGTTCCGTCCCGAGAACGTCGTCGCCGAGCTGGCGGAAGCCGGT

CTGCGGCAGACGCATTGGTGGACCGATCCGGCCGGGGATTTCGGGTTGTC

GCTGGCGGTGCGGTGA)

In some embodiments, the egtE gene is a C—S lyase and comprises the nucleotide sequence of SEQ ID NO: 4 (pyridoxal-phosphate-dependent transferase [*Mycobacterium smegmatis* str. MC2 155], ACCESSION ABK70212, VERSION ABK70212.1 GI:118169316:

GTGATGCTCGCGCAGCAGTGGCGTGACGCCCGTCCCAAGGTTGCCGGGTT

GCACCTGGACAGCGGGGCATGTTCGCGGCAGAGCTTCGCGGTGATCGACG

-continued

CGACCACCGCACACGCACGCCACGAGGCCGAGGTGGGTGGTTATGTGGCG

GCCGAGGCTGCGACGCCGGCGCTCGACGCCGGGCGGGCCGCGGTCGCGTC

GCTCATCGGTTTTGCGGCGTCGGACGTGGTGTACACCAGCGGATCCAACC

ACGCCATCGACCTGTTGCTGTCGAGCTGGCCGGGGAAGCGCACGCTGGCC

TGCCTGCCCGGCGAGTACGGGCCGAATCTGTCTGCCATGGCGGCCAACGG

TTTCCAGGTGCGTGCGCTACCGGTCGACGACGACGGGCGGGTGCTGGTCG

ACGAGGCGTCGCACGAACTGTCGGCCCATCCCGTCGCGCTCGTACACCTC

ACCGCATTGGCAAGCCATCGCGGGATCGCGCAACCCGCGGCAGAACTCGT

CGAGGCCTGCCACAATGCGGGGATCCCCGTGGTGATCGACGCCGCGCAGG

CGCTGGGGCATCTGGACTGCAATGTCGGGGCCGACGCGGTGTACTCATCG

TCGCGCAAGTGGCTCGCCGGCCCGCGTGGTGTCGGGGTGCTCGCGGTGCG

GCCCGAACTCGCCGAGCGTCTGCAACCGCGGATCCCCCCGTCCGACTGGC

CAATTCCGATGAGCGTCTTGGAGAAGCTCGAACTAGGTGAGCACAACGCG

GCGGCGCGTGTGGGATTCTCCGTCGCGGTTGGTGAGCATCTCGCAGCAGG

GCCCACGGCGGTGCGCGAACGACTCGCCGAGGTGGGGCGTCTCTCTCGGC

AGGTGCTGGCAGAGGTCGACGGGTGGCGCGTCGTCGAACCCGTCGACCAA

CCCACCGCGATCACCACCCTTGAGTCCACCGATGGTGCCGATCCCGCGTC

GGTGCGCTCGTGGCTGATCGCGGAGCGTGGCATCGTGACCACCGCGTGTG

AACTCGCGCGGGCACCGTTCGAGATGCGCACGCCGGTGCTGCGAATCTCG

CCGCACGTCGACGTGACGGTCGACGAACTGGAGCAGTTCGCCGCAGCGTT

GCGTGAGGCGCCCTGA)

In some embodiments, the gene encoding the FAD synthetase comprises the nucleotide sequence of SEQ ID NO: 5 (*Corynebacterium ammoniagenes* gene for FAD synthetase, complete cds, ACCESSION D37967, VERSION D37967.1 GI:840670:

GTGGATATTTGGTACGGAACAGCAGCAGTCCCAAAAGACTTAGACAACAG

TGCAGTCACCATTGGTGTCTTCGACGGCGTGCATCGCGGGCATCAGAAAT

TGATTAATGCCACTGTTGAAAAAGCACGCGAGGTGGGCGCGAAAGCCATC

ATGGTTACTTTTGACCCGCACCCAGTGTCCGTGTTTCTCCCGCGCCGTGC

GCCGCTGGGGATTACTACCTTGGCTGAGCGCTTTGCGCTGGCGGAAAGCT

TTGGCATTGATGGCGTGCTAGTCATTGATTTTACCCGCGAACTCTCTGGT

ACTTCGCCGGAGAAGTACGTGGAATTTCTTCTAGAAGACACGCTGCATGC

CTCACACGTGGTGGTCGGAGCTAACTTTACTTTTGGGGAAAATGCCGCCG

GCACCGCAGATTCCTTGCGGCAGATTTGCCAGTCGCGTTTGACCGTTGAT

GTCATCGACTTGCTTGACGATGAAGGCGTGAGGATCTCTTCCACGACCGT

GCGCGAGTTTCTATCTGAAGGAGATGTTGCGCGAGCCAACTGGGCTTTGG

GGCGGCACTTTTATGTCACAGGTCCAGTAGTCCGTGGTGCTGGCCGCGGA

GGCAAGGAGCTGGGATTTCCCACGGCGAATCAGTACTTTCACGATACTGT

CGCTTTTGCCTGCCGATGGGGTCTATGCCGGCTGGTTGACCATTTTGCCCA

CCGAGGCACCCGTAAGCGGGAATATGGAACCTGAGGTGGCTTATGCCGCC

GCTATTTCAGTGGGAACCAACCCGACCTTTGGCGATGAGCAGCGTTCTGT

GGAGTCTTTTGTACTCGATAGAGATGCTGATCTTTATGGTCACGACGTCA

AAGTGGAATTTGTTGACCACGTGCGGGCAATGGAAAAGTTTGACTCCGTC

GAGCAGCTTTTGGAAGTCATGGCTAAAGACGTGCAGAAAACCCGCACTTT

GCTAGCTCAGGATGTGCAAGCACATAAGATGGCGCCTGAGACCTACTTTC

TACAAGCAGAAAGCTAA

In some embodiments, the gene encoding SAM synthetase comprises the nucleotide sequence of SEQ ID NO: 6 (*E. coli* metK gene coding for S-adenosylmethionine synthetase. ACCESSION K02129 REGION: 86 . . . 1240, VERSION K02129.1 GI:146838:

ATGGCAAAACACCTTTTTACGTCCGAGTCCGTCTCTGAGGGCCATCCTGA

CAAAATTGCTGACCAAATTTCTGATGCCGTTTTAGACGCGATCCTCGAAC

AGGATCCGAAAGCACGCGTTGCTTGCGAAACCTACGTAAAAACCGGCATT

GGTTTTAGTTGGCGGCGAAATCACCACCAGCGACCTTGGGTAGACATCGA

AGAGATCACCCGTAACACCGTTCGCGAAATTGGCTATGTGCATTCCGACA

TGGGCTTTGACGCTAACTCCTGTGCGGTTCTGAGCGCTATCGGCAAACAG

TCTCCTGACATCAACCAGGGCGTTGACCGTGCCGATCCGCTGGAACAGGG

CGCGGGTGACCAGGGTCTTGATGTTTCGGCTACGCAACTAATGAAACCGA

CGTGCCTGATGCCAGCACCTATCACCTATGCCCACCGTCTGGTACAGCGT

CAGGCTGAAGTGCGTAAAAACGGCACTCTGCGTGTGCGCCCGGACGCGAA

AAGCCAGGTGACTTTTAGCTATGACGACGGCAAAATCGTTGGTATCGATG

CTGTCGTGCTTTCCACTCAGCACTCTGAAGAGATCGACCAGAAATCGCTG

CAAGAAGCGGTAATGGAAGAGATCATCAAGCCAATTCTGCCCGCTGAATG

GCTGACTTCTGCCACCAAATTCTTCATCAACCCGACCGGTCGTTTCGTTA

TCGGTGGCCCAATGGGTGACTGCGGTCTTACTGGTCGTAAAATTATCGTT

GATACTACCGGCGGCATGGCGCGTCACGGTGGCGGTGCATTCTCTGGTAA

AGATCCATCAAAAGTGGACCGTTCCGCAGCCTACGCAGCACGTTATGTCG

CGAAAAACATCGTTGCTGCTGGCCTGGCCGATCGTTGTGAAATTCAGGTT

TCCTACGCAATCGGCCTGGCTGAACCGACCTCCATCATGGTAGAAACTTT

CGGTACTGAGAAAGTGCCTTCTGAACAACTGACCCTGCTGGTACGTGAGT

TCTTCGACCTGCCAATCGGTCTGATTCAGATGCTGGATCTGCTGCACCCG

ATCTACAAAGAAACCGCAGCATACGGTCACTTTGGTCGTGAACATTTCCC

GTGGGAAAAAACCGACAAAGCGCAGCTGCTGCGCGATGCTGCCGGTCTGA

AGTAA

As one of ordinary skill in the art is aware, homologous genes for the enzymes could be obtained from other species and could be identified by homology searches, for example through a protein BLAST search, available at the National Center for Biotechnology Information (NCBI) internet site (www.ncbi.nlm.nih.gov). Genes associated with the invention can be PCR amplified from DNA from any source of DNA which contains the given gene. In certain embodiments, genes are obtained by polymerase chain reaction (PCR) using genomic DNA (gDNA) templates. In some embodiments, genes associated with the invention are synthetic. Any means of obtaining a gene encoding the enzymes associated with the invention are compatible with the instant invention.

As used herein, to express a gene means that the cell produces either the full length polypeptide encoded by the gene or a functional fragment of the full length polypeptide. The term "functional" when used in conjunction with "fragment" refers to a polypeptide which possesses a biological activity that is substantially similar to a biological activity of the entity or molecule of which it is a fragment thereof. By "substantially similar" in this context is meant that at least 25%, at least 35%, at least 50% of the relevant or desired biological activity of a corresponding wild-type peptide is retained. For example, a functional fragment of polypeptide retains enzymatic activity that is substantially similar to the enzymatic activity of the full length polypeptide encoded by a gene expressed in the cell.

In the instant case, a functional fragment of a polypeptide encoded by the egtE gene would be peptide that can catalyze the cleavage of a C—S bond in the product of oxidative coupling between hercynine and cysteine, i.e., conversion of intermediate

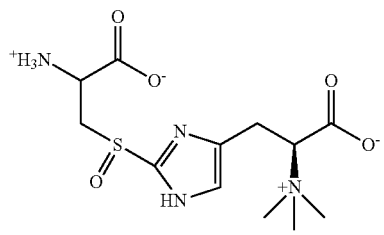

to ergothioneine. A functional fragment of a polypeptide encoded by the ovoA gene or ncEgt-1 gene would be a peptide that can catalyze the formation of

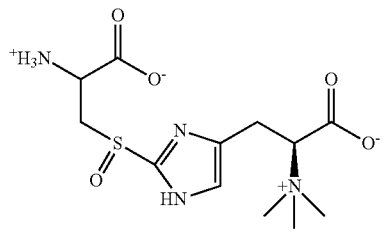 [SMILES: C[N+](C)(C)[C@@H](Cc1c[nH]c(S(=O)CC([NH3+])C(=O)[O-])n1)C(=O)[O-]]

from hercynine and cysteine. A functional fragment of a polypeptide encoded by the egtD gene would be a peptide that can catalyze the N-methylation of histidine to produce hercynine. A functional fragment of a polypeptide encoded by the SAM gene would be a peptide that can catalyze the conversion of methionine and ATP into S-adenosylmethionine. A functional fragment of a polypeptide encoded by the FAD synthetase gene would be a peptide that can catalyze the formation of FAD. Such functional fragments can be assessed by the methods as disclosed herein in the Examples.

In some embodiments, one or more of the genes described herein is expressed in a recombinant expression vector or plasmid. As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, *Molecular Cloning: A Laboratory Manual,* 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

In some embodiments, the vector is pETDuet vector.

In some other embodiments, the vector is pACYDuet vector.

In some other embodiments, the vector is pASK-IBA vector.

Without limitations, the genes described herein can be included in one vector or separate vectors. For example, the ovoA gene or the ncEgt-1 gene and the egtE gene can be included in the same vector; or the egtE gene and the gene encoding the FAD synthetase gene can be included in the same vector; or the ovoA gene or the ncEgt-1 gene, the egtE gene, and the gene encoding a FAD synthetase can be included in the same vector; or the egtD gene and the gene encoding the SAM synthetase can be included in the same vector.

In some embodiments, the ovoA gene or the ncEgt-1 gene, the egtE gene, and the gene encoding a FAD synthetase can be included in a first vector; and the egtD gene, the ovoA gene or the ncEgt-1 gene, and the egtE gene can be included in a second vector.

In some embodiments, one or more of the recombinantly expressed gene can be integrated into the genome of the cell.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

Some aspects provided herein are directed to cell culture medium or supernatant collected from culturing the cell described herein.

Other aspects provided herein are directed to a method, comprising culturing in cell culture medium the cell described herein.

Various aspects described herein related to a method, which comprises recombinantly expressing in a cell one or more genes of the ergothioneine biosynthetic pathway and one or more genes of the ovothiol biosynthetic pathway.

Some aspects provided herein are directed to a method for preparing ergothioneine.

In some embodiments, the method comprised recombinantly expressing in a cell: (i) EgtA protein or a functional fragment thereof retaining enzymatic activity; (ii) EgtB protein or a functional fragment thereof retaining enzymatic activity; (iii) EgtC protein or a functional fragment thereof retaining enzymatic activity; (iv) EgtD protein or a functional fragment thereof retaining enzymatic activity; and (v) EgtE protein or a functional fragment thereof retaining enzymatic activity and a gene encoding FAD synthetase or a functional fragment thereof retaining enzymatic activity.

In some embodiments, the method comprises recombinantly expressing in a cell: (i) an OvoA protein, a NcEgt1 protein or a functional fragment thereof retaining enzymatic activity; (ii) an EgtE protein or a functional fragment thereof retaining enzymatic activity; and (iii) a FAD synthetase or a functional fragment thereof retaining enzymatic activity.

In some embodiments, the method comprises recombinantly expressing in a cell: (i) an EgtD protein or a functional fragment thereof retaining enzymatic activity; (ii) an OvoA protein, a NcEgt1 protein or a functional fragment thereof retaining enzymatic activity; (iii) an EgtE protein or a functional fragment thereof retaining enzymatic activity; and (iv) a FAD synthetase or a functional fragment thereof retaining enzymatic activity. In some further embodiments of this application, the cell further expresses a SAM synthetase or a functional fragment thereof retaining enzymatic activity.

In some embodiments, the method comprises recombinantly expressing in a cell: (i) a ovoA or a ncEgt-1 gene; and (ii) a egtE gene and a FAD synthetase gene.

As discussed herein, the inventors have also discovered that synthesis of ergothioneine can be further simplified by starting with hercynine and producing ergothioneine in the transformed cell. Accordingly, in some embodiments, the method comprises recombinantly expressing in a cell: (i) a egtD gene; (ii) a ovoA gene or ncEgt-1 gene; and (iii) a egtE gene and a FAD synthetase gene. In some embodiments, the method further comprises recombinantly expressing from the cell a gene encoding a S-adenosylmethionine (SAM) synthetase.

In some embodiments, the method described herein further comprises culturing in cell culture medium the cell described herein.

In some embodiments, the method described in any one of the aspects or embodiments presented herein comprises feeding hercynine or histidine to the cell. For example, if the cell does not express (recombinantly or otherwise) the egtD gene, the cells can be fed hercynine, i.e., the culture medium can be supplemented with hercynine. In another example, if the cell expresses (recombinantly or otherwise) the egtD gene then the cells can be fed histidine, i.e., the culture medium can be supplemented with histidine. Expression of the egtD gene allows the cell to convert histidine to hercynine which can then be used by the polypeptide expressed by the ovoA gene or the ncEgt-1 gene.

In some embodiments, the method described herein further comprises collecting cell culture medium or supernatant after culturing the cell described herein.

In some embodiments, the method described herein comprises in vitro reactions using either pure enzymes or lysates from cells expressing these enzymes, e.g., a lysate obtained from a cell described herein. Accordingly, in some embodiments, the method for producing ergothioneine comprises: (i) incubating histidine or hercynine with a reaction mixture comprising recombinantly expressed EgtA protein or a functional fragment thereof retaining enzymatic activity, EgtB protein or a functional fragment thereof retaining enzymatic activity, EgtC protein or a functional fragment thereof retaining enzymatic activity, EgtD protein or a functional fragment thereof retaining enzymatic activity, and EgtE protein or a functional fragment thereof retaining enzymatic activity; and (ii) isolating ergothioneine from the enzymatic mixture.

In some embodiments, a method for preparing ergothioneine comprises: (i) incubating hercynine with a reaction mixture comprising recombinantly expressed: (a) OvoA protein, NcEgt1 protein or a functional fragment thereof retaining enzymatic activity and (b) EgtE protein of a functional fragment thereof retaining enzymatic activity; and (ii) isolating ergothioneine from the enzymatic mixture.

In some embodiments, a method for preparing ergothioneine comprises: (i) incubating histidine with a reaction mixture comprising recombinantly expressed: (a) EgtD protein or a functional fragment thereof retaining enzymatic activity, (b) OvoA protein, NcEgt1 protein or a functional fragment thereof retaining enzymatic activity, and (c) EgtE protein or a functional fragment thereof retaining enzymatic activity; and (ii) isolating ergothioneine from the enzymatic mixture.

In some embodiments, the reaction mixture comprises a cell lysate from a cell described herein. Accordingly, in some embodiments, the reaction mixture comprises a cell lysate (e.g., cell-free lysate) from a cell described herein.

In some embodiments, the reaction mixture further comprises methoinenine or cysteine.

In some embodiments, the reaction mixture is supplemented with an iron salt.

In some embodiments, the method described herein further comprises recovering ergothioneine from the cell, from the culture medium in which the cell is grown, or the reaction mixture.

The cell, e.g., transformed cell, can be cultured in conventional cell cultures or fermentation bioreactors. The cell can be cultured by any culturing or fermentation process including, but not limited to, batch, fed-batch, cell recycle, and continuous fermentation. The cell according to the invention can be cultured in media of any type (rich or minimal) and any composition. As would be understood by one of ordinary skill in the art, in some embodiments, routine optimization would allow for use of a variety of types of media. The selected medium can be supplemented with various additional components. Some non-limiting examples of supplemental components include hercynine, histidine, antibiotics, IPTG or other inducers for gene induction, and ATCC Trace Mineral Supplement. Similarly, other aspects of the medium and growth conditions of the cells of the invention can be optimized through routine experimentation. For example, pH and temperature are non-limiting examples of factors which can be optimized. In some embodiments, factors such as choice of media, media supplements, and temperature can influence production levels of ergothioneine. In some embodiments the concentration and amount of a supplemental component can be optimized. In some embodiments, how often the media is supplemented with one or more supplemental components, and the amount of time that the media is cultured before harvesting ergothioneine is optimized.

According to aspects described herein, high titers of ergothioneine are produced through the recombinant expression of genes associated with the invention, in a cell or cell-free lysate. As used herein "high titer" refers to a titer in the milligrams per liter (mg $L^{-1}$) scale or higher. The titer produced for a given product will be influenced by multiple factors including choice of media. In some embodiments the titer for production of ergothioneine is at least 1000 mg $L^{-1}$.

In certain aspects, liquid cultures used to grow cells associated with the embodiments described herein are housed in any of the culture vessels known and used in the art. In some embodiments large scale production in an aerated reaction vessel such as a stirred tank reactor is used to produce large quantities of ergothioneine.

After the ergothioneine is produced by the transformed cell, the ergothioneine can accumulate in the culture medium and can be collected or recovered therefrom. To "collect" a product such as ergothioneine can simply refer to collecting the biomass from the fermentation bioreactor and need not imply additional steps of separation, recovery, or purification. For example, the step of collecting can refer to removing the entire culture (i.e., the transformed cells and the fermentation medium) from the bioreactor, and/or removing the transformed cells containing ergothioneine from the bioreactor. The term "recovering" or "recover", as used herein with regard to recovering ergothioneine refers to performing additional processing steps to obtain ergothioneine at any level of purity. These steps can be followed by further purification steps. For example, ergothioneine can be recovered from the biomass by a technique that includes, but is not limited to, the following steps: lysing the cells solution, collection and washing of the remaining solids containing ergothioneine, resuspension of the washed solids in an appropriate buffer or solution, and enrichment of ergothioneine from the solution along with subsequent purifications by chromatography.

In some embodiments, the ergothioneine is recovered in substantially pure form. As used herein, "substantially pure" refers to a purity that allows for the effective use of the ergothioneine as a compound for commercial sale.

In some embodiments, the ergothioneine products are preferably separated from the production organism and other culture medium constituents or the reaction mixture. Methods to accomplish such separation are known to one of skill in the art. For example, separation techniques include, but are not limited to, the combination of ion-exchange chromatography and HPLC purification.

Aspects of the invention include strategies to optimize production of ergothioneine from a cell. Optimized production of ergothioneine refers to producing a higher amount of ergothioneine following pursuit of an optimization strategy than would be achieved in the absence of such a strategy. In some embodiments, optimization includes increasing expression levels of one or more genes described herein through selection of appropriate promoters and ribosome binding sites. In some embodiments this includes the selection of high-copy number plasmids, or low or medium-copy number plasmids. In some embodiments the plasmid is a medium-copy number plasmid such as pETDuet. Other plasmids that can be used in the cells and methods described herein include pCDFDuet-1, pACYCDuet-1, pASK-IBA, and pCOLADuet-1. The step of transcription termination can also be targeted in some embodiments for regulation of gene expression, through the introduction or elimination of structures such as stem-loops.

In some embodiments, a cell that has been optimized for production of ergothioneine is used. In some embodiments, screening for mutations that lead to enhanced production of ergothioneine is conducted through a random mutagenesis screen, or through screening of known mutations. In other embodiments, shotgun cloning of genomic fragments is used to identify genomic regions that lead to an increase in production of ergothioneine, through screening cells or organisms that have these fragments for increased production of ergothioneine. In some cases one or more mutations are combined in the same cell or organism.

Optimization of protein expression can also require in some embodiments that a gene encoding an enzyme be modified before being introduced into a cell such as through codon optimization for expression in a bacterial cell. Codon usages for a variety of organisms can be accessed in the Codon Usage Database (website: kazusa.or.jp/codon/).

In some embodiments, protein engineering can be used to optimize expression or activity of one or more enzymes associated with the invention. In certain embodiments a protein engineering approach could include determining the 3D structure of an enzyme or constructing a 3D homology model for the enzyme based on the structure of a related protein. Based on 3D models, mutations in an enzyme can be constructed and incorporated into a cell or organism, which could then be screened for an increased production of ergothioneine. In some embodiments production of ergothioneine in a cell is increased through manipulation of enzymes that act in the same pathway as the enzymes associated with the pathways described herein. For example, in some embodiments it can be advantageous to increase expression of an enzyme or other factor that acts upstream of a target enzyme such as an enzyme associated with any one or more of the pathways described herein. In some embodiments, this is achieved by over-expressing the upstream factor using any standard method.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, "genetic elements" refers to defined nucleic acids (generally DNA or RNA) having expressible coding sequences for products such as proteins, apoproteins, or antisense nucleic acid constructs, which can perform or control pathway enzymatic functions. The expressed proteins can function as enzymes, repress or depress enzyme activity, or control expression of enzymes. The nucleic acids encoding these expressible sequences can be either chromosomal, e.g. integrated into a nonhuman organism's chromosome by homologous recombination, transposition, or some other method, or extrachromosomal (episomal), e.g. carried by plasmids, cosmids, etc. Genetic elements include control elements. Many other genetic elements are known in the art. See, for example, U.S. Pat. Nos. 4,980,285; 5,631,150; 5,759,828; 5,888,783 and, 5,919,670.

As used herein, the term "genetic manipulation" refers to the purposeful alteration of polynucleotide sequences either by in vitro techniques, in vivo techniques, or a combination of both in vitro and in vivo techniques. "Genetic manipulation" includes the introduction of heterologous polynucleotide sequences into nonhuman organisms, either into the chromosome or as extrachromosomally replicating elements, the alteration of chromosomal polynucleotide sequences, the addition and/or replacement of transcriptional and/or translational regulatory signals to chromosomal or plasmid encoded genes, and the introduction of various insertion, deletion and replacement mutations in genes of interest. Methods for in vitro and in vivo genetic manipulations are widely known to those skilled in the art. See, for example, Sambrook et al., *Molecular Cloning: A Laboratory Manual,* 2nd Ed., Cold Spring Harbor Press (1989) and U.S. Pat. Nos. 4,980,285; 5,631, 150; 5,759,828; 5,888,783 and, 5,919,670.

As used herein, "operably linked" refers to juxtaposition such that the normal function of the components can be performed. Thus, a coding sequence "operably linked" to control sequences refers to a configuration wherein the coding sequences can be expressed under the control of these sequences. Such control may be direct, that is, a single gene associated with a single promoter, or indirect, as in the case where a polycistronic transcript is expressed from a single promoter. See, for example, U.S. Pat. Nos. 4,980,285; 5,631,150; 5,707,828; 5,759,828; 5,888,783 and, 5,919,670, and Sambrook et al., *Molecular Cloning: A Laboratory Manual,* 2nd Ed., Cold Spring Harbor Press (1989).

As used herein, "over-expression" refers to gene expression. Genes and gene products can be overexpressed. Such gene products include RNAs, proteins and enzymes. On the other hand, "overproduce" refers to cellular products that accumulate, especially cell products that are to be harvested for some specific use. Thus proteins, materials (such as polymers), and metabolites (such as amino acids) are overproduced. Proteins may be either overexpressed (if referring to the control of gene expression) or overproduced (if referring to the accumulation of the proteins). By "over production" of ergothioneine, it is intended that a cell "overproducing" ergothioneine produces more molecules of ergothioneine for each cell under a given set of growth conditions than a similar cell not "over producing" ergothioneine.

As used herein, the term "promoter" has its art-recognized meaning, denoting a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. Useful promoters include constitutive and inducible promoters. Many such promoter sequences are known in the art. See, for example, U.S. Pat. Nos. 4,980,285; 5,631,150; 5,707,828; 5,759,828; 5,888, 783; 5,919,670, and, Sambrook et al, *Molecular Cloning: A Laboratory Manual,* 2nd Ed., Cold Spring Harbor Press (1989). Other useful promoters include promoters which are neither constitutive nor responsive to a specific (or known) inducer molecule. Such promoters may include those that respond to developmental cues (such as growth phase of the culture or stage of cell differentiation), or environmental cues (such as pH, osmoticum, heat, or cell density). A heterologous promoter is a promoter which is not naturally linked to the gene. Heterologous promoters may be from the same or different species. For example, a heterologous promoter may be a promoter from the same organism as the gene but naturally found linked to a different gene.

As used herein, the term "transgene" when used in reference to polynucleotide sequences, refers to polynucleotide sequences not naturally present in a cell. Thus the term "transgene" includes, for example, the promoter of gene A operably joined to structural gene B, when A and B genes are from the same organism, as well as the case in which a polynucleotide sequence of one species is transferred to a cell of a different species (or strain). The term "transgene" also includes clones of transgenes which have been so modified. See, U.S. Pat. Nos. 4,980,285; 5,631,150; 5,707, 828; 5,759,828; 5,888,783 and, 5,919,670.

As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

As used herein, the term "cell type," refers to any cell, regardless of its source or characteristics.

As used herein, the term "transformed cell lines," refers to cell cultures that have been transformed into continuous cell lines with the characteristics as described herein.

As used herein, the term "transformed nonhuman organisms" includes the primary transformed subject cell and its transformed progeny. The nonhuman organism can be prokaryotic or eukaryotic. Thus "transformants" or "transformed cells" includes the primary subject cell, transformed with the transgene, and cultures derived therefrom, without regard for the number of transfers. It is also understood that all progeny may not be precisely identical in DNA content, due to deliberate or inadvertent mutations and/or modifications. Mutant progeny which have the same functionality as screened for in the originally transformed cell are included. Where distinct designations are intended, it will be clear from the context. See, for example, U.S. Pat. Nos. 4,980, 285; 5,631,150; 5,707,828; 5,759,828; 5,888,783; 5,919, 670, and, Sambrook et al., *Molecular Cloning: A Laboratory Manual,* 2nd ed., 60 Cold Spring Harbor Press (1989).

As used herein, the term "isolated" means altered "by the hand of man" from the natural state. An "isolated" composition or substance is one that has been changed or removed from its original environment, or both. For example, a polynucleotide or a polypeptide naturally present in a cell or living animal is not "isolated," but the same polynucleotide or polypeptide separated from the coexisting materials of its natural state is "isolated," as the term is employed herein.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

To the extent not already indicated, it will be understood by those of ordinary skill in the art that any one of the various embodiments herein described and illustrated can be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Production of Ergothioneine Through Metabolic Engineering (In Vitro Enzymatic Approach)

Identification of ergothioneine biosynthetic gene cluster. Ergothioneine and ovothiol (5 & 7, FIG. 1) are two thiol-imidazole containing metabolites isolated from ergot by Tanret in 1909.[1] The presence of ergothioneine specific transporter in human[2] allows us to enrich ergothioneine from diets to millimolar concentrations in a few organs (e.g., liver, kidney, central nervous system and red blood cells).[3] Unlike other thiols, the equilibrium between the thiolate and thione forms of the thiol-imidazole side-chain in ergothioneine and ovothiol favors predominantly the thione form (e.g., 5 in FIG. 1A),[3,4] which renders them being much more stable to oxidation relative to other thiols (e.g., glutathione).[4a] The unique ergothioneine redox properties[4a,5] allow it to protect the hemoglobin from being oxidized in red blood cells, prevent the cataract formation in the lens.[6] In addition, it can function as a metal chelator for cellular metal detoxifications. Currently, ergothioneine is widely applied as one of the key components in many commercial products (anti-aging cosmetics, preservatives, dietary supplements, hair and nail growth stimulating products, etc.) with a market size of billions of dollars.

Using a combination of bioinformatic tools for genome-wide analysis and biochemical characterization, the ergothioneine biosynthetic pathway (FIG. 1) was proposed by Seebeck in 2010.[7] When the structure of ergothioneine (5) is analyzed, it is clear that it is a histidine derivative with methylation and thiolketone functional groups. Seebeck analyzed the genomes of three ergothioneine biosynthetic organisms, *Mycobacterium avium*, *Mycobacterium smegmatis*, and *Neurospora crassa*. In *M. avium* genome, there are 78 genes annotated as methyltransferases.[8] Among those 78 methyltransferases, there are only 29 having homologs in *N. crassa*. Because *E. coli* and *Bacillus subtilis* do not produce ergothioneine, among the 29 remaining methyltransferases, those with homologs in either *E. coli* or *B. subtilis* were then further eliminated. By applying the positive and negative selection rules in genome-wide analysis using bioinformatic tools, Seebeck narrows the number of methyltransferases down to 10. Because genes for the biosynthesis of secondary metabolites in bacteria tend to cluster into operon structures, by further analyzing the neighborhood of the remaining 10 methyltransferases, he narrows it down to one candidate in *M. smegmatis* (MSMEG_6247, now designated as EgtD in FIG. 1). Besides the methyltransferase (EgtD) in the gene cluster, EgtA (MSMEG_6250) encodes a γ-glutamylcysteine ligase; EgtB has unknown function; EgtC is a amidotransamidase; EgtE seems to be a PLP dependent enzyme. In addition, Seebeck has confirmed EgtA, EgtB, EgtC, and EgtD functions by demonstrating activities in vitro. The proposed C—S lyase activity (EgtE) was not confirmed because according to Seebeck, EgtE cannot be expressed despite extensive efforts from them.[9]

Due to the significant similarity between ergothioneine and ovothiol, it was hypothesized that an EgtB homolog in ovothiol producing strains might be responsible for the C—S bond formation in ovothiol biosynthesis. Indeed, such a homolog (OvoA, FIG. 1B) in an ovothiol producing strain, *Erwinia tasmaniensis*, was identified by search EgtB homologs in *E. tasmaniensis* genome. After OvoA was overexpressed and purified in *E. coli*, the purified enzyme does catalyze the coupling between histidine and cysteine to form a sulfoxide (6, FIG. 1B).[10] The rest of the ovothiol biosynthetic pathway remains to be identified.

There is a high demand for ergothioneine due to its wide application as one of the key components in many commercial products. However, the current chemical synthetic scheme is not efficient,[11] and isolation from natural sources (e.g., mushroom) is not practical due to its low natural abundance. The identification of ergothioneine and ovothiol biosynthetic gene cluster set the stage for more detailed mechanistic studies of ergothioneine and ovothiol biosynthesis and their production through metabolic engineering. For ergothioneine production through metabolic engineering following the scheme in FIG. 1, there are three issues:

(i) The EgtB activity is low. EgtB is proposed to be a mononuclear non-heme iron enzyme. The current activity is low. We either need to improve its activity or find an enzyme with a better activity.

(ii) EgtE protein cannot be overexpressed. To date, there has no literature report on successful EgtE overexpression. In order to reconstitute ergothioneine biosynthetic pathway, this issue has to be resolved.

(iii) The current ergothioneine biosynthetic pathway needs to be optimized. The natural ergothioneine biosynthetic pathway, especially the oxidative C—S bond formation step (EgtB catalysis) needs to be optimized. In addition, following the pathway in FIG. 1A, there is a competition between the biosyntheses of ergothioneine and glutathione.

For the natural ergothioneine biosynthetic pathway in FIG. 1, EgtB oxidatively couples hercynine (2) and γ-Glu-Cys to form 3. The glutamate in 3 is then hydrolyzed by another enzyme EgtC to form EgtE substrate 4. If an enzyme that can catalyze the direct oxidative coupling of hercynine (2) and Cys (red arrow in FIG. 1) can be identified, it will offer at least two advantages: 1) It will cut the ergothioneine biosynthetic pathway by two steps; 2) It will eliminate the competition of ergothioneine and glutathione biosynthesis because γ-Glu-Cys is also the substrate in glutathione biosynthetic pathway. Because glutathione is one of the key molecules used to regulate the intracellular reduction potentials and present in mM concentrations, eliminating such a competition will relieve cellular stress under high level ergothioneine production conditions and offer significant advantages for high level ergothioneine production through metabolic engineering.

Figure 2:
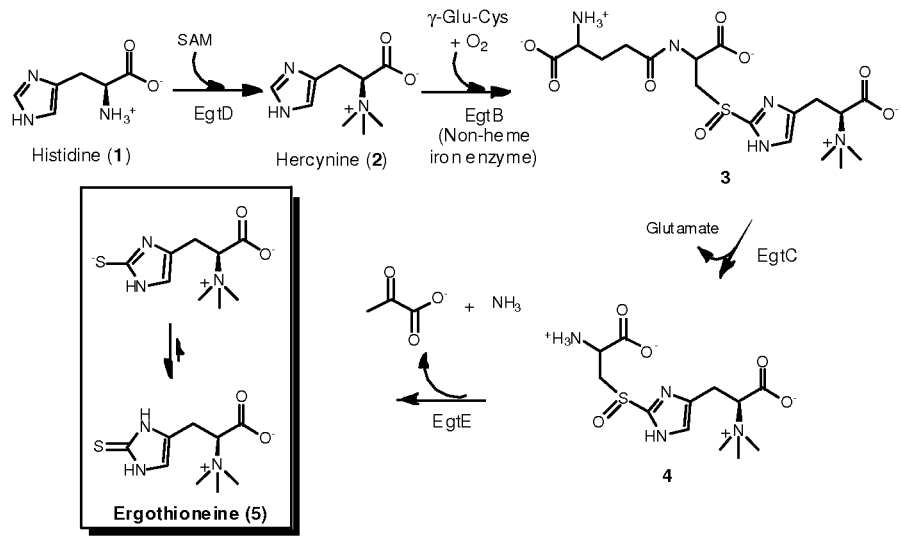
FIG. 2 is a schematic representation of ergothioneine production according to an embodiment the method described herein. Pathway A relies on successful production of EgtE and improvement of EgtB activity; Pathway B relies on the discovery of enzymes (e.g., OvoA and NcEgt1) capable of 2 to 4 conversion and the successful production of EgtE.
Figure 2:
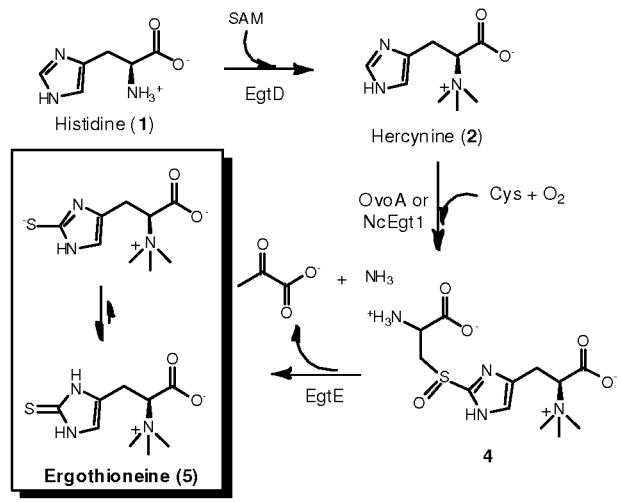

This invention addresses all of the above problems, which lead to the new ergothioneine biosynthetic pathway, an embodiment of which is shown in FIG. 2.

Improving the activities of mono-nuclear non-heme iron enzymes. As an essential step toward improving those mono-nuclear non-heme iron enzymes (e.g., EgtB, OvoA), we have developed at least two different activity assays, which are then used to guide our efforts in improving the activities of these enzymes.

Figure 3:
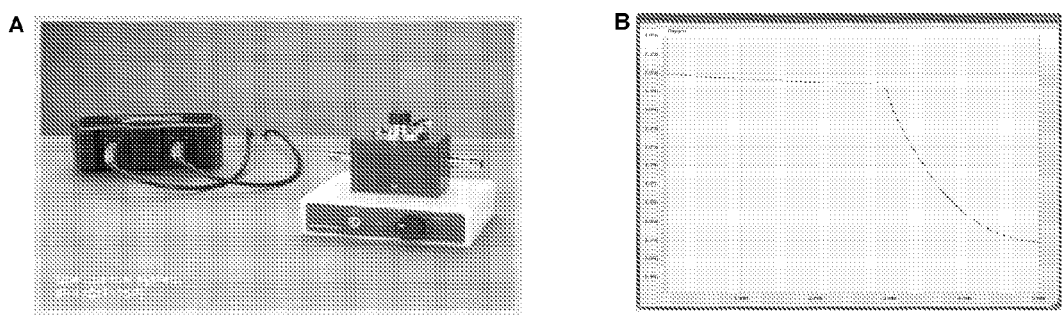
FIG. 3 shows two different assays for EgtB and OvoA catalysis.
Figure 3:
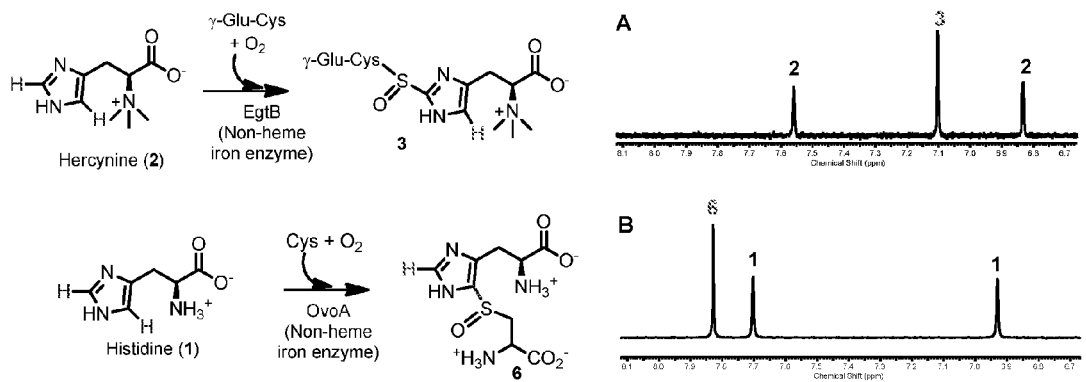

Activity assays. Two different assays were developed for both EgtB and OvoA catalysis (FIG. 3). Both EgtB and OvoA are proposed to be oxidases,[9-10] which catalyze the oxidative coupling between His and Cys to form the C—S bond. At the same time, sulfur is oxidized to sulfoxide. The overall process is a four-electron oxidation process (FIG. 1) similar to the case of the isopenicillin N synthase.[12] In the initial report by Seebeck, they monitored the reaction by monitoring the absorption changes at 260 nm because the oxidative products (3 or 6, FIG. 1) have absorptions in this region. However, it is not very sensitive. Oxygen is needed because there was no detectable product formation under anaerobic conditions. Based on this feature, we developed the EgtB and OvoA activity assays by monitoring the oxygen consumption rate (FIG. 3-I-B) using the NeoFoxy oxygen electrode (FIG. 3-I-A). This assay (FIG. 3-I-B) was used as the routine assay to optimize the conditions for EgtB and OvoA activities.

For oxygenase or oxidase-catalyzed reaction, potential problems include the presence of side-reactions, non-productive oxygen consumption, or oxidative inactivation of enzyme itself. Multiple activity assays will provide useful information to analyze those situations. To achieve this goal, besides the oxygen consumption assay, we have also developed a $^1$H-NMR assay to directly monitor the product formation (FIG. 3-II). In $^1$H-NMR, the chemical shifts of the imidazole H-atoms in both the products (3 and 6, FIG. 3-II) and the substrates (1 and 2) are well-separated from the rest of the reaction mixture. Thus, the reaction mixture can be analyzed routinely without the need of a product separation. In FIG. 3-II-B (OvoA catalysis), the signals with chemical shifts at 6.93 ppm and 7.70 ppm are assigned to the two histidine imidazole H-atoms. The signal at 7.83 ppm is from the imidazole H-atom of the oxidative coupling product 6. While for the oxidative product 3 (EgtB catalysis), its imidazole H-atom has a chemical shift of 7.10 ppm (FIG. 3-II-B). Thus, the combination use of oxygen consumption assay and $^1$H-NMR assay allow us to obtain several mechanistic features: 1) the ratio between oxygen consumption and production formation; 2) product C—S bond region-selectivity; 3) the presence of reactions other than the proposed oxidative C—S bond formation Improved OvoA activity. Because EgtB and OvoA are proposed to be mono-nuclear non-heme iron enzymes, if they are ferrous enzymes, they might be inactivated during the catalytic turnover processes. Using oxygen consumption assay, we have improved OvoA activity ($k_{cat}$ of 572±20 min$^{-1}$) by 300-fold relative to that reported by Seebeck,[10] which is the result of a combination of several factors: 1) we purified OvoA anaerobically instead of aerobically to minimize the chance of OvoA inactivation during the purification process; 2) anaerobic reconstitution of purified OvoA with $Fe^{2+}$; 3) include ascorbate in the reaction buffer to reduce $Fe^{3+}$ back to $Fe^{2+}$ if some OvoA is indeed inactivated by oxidizing $Fe^{2+}$ to $Fe^{3+}$ during the catalytic turnover process. Without wishing to be bound by a theory, these strategies can be also be applied to EgtB and NcEgt1 proteins.

These initial results points directions at future work on improving EgtB and OvoA in vivo activities, including 1) Supplementing the culture medium with Fe. 2) Because the uptake and maturation of the metallo-enzymes (EgtB or OvoA) is essential for maximal in vivo efficacy, Fe uptake system can be used for producing an ergothioneine production strain (e.g., siderophore biosynthetic gene clusters).

Figure 4:
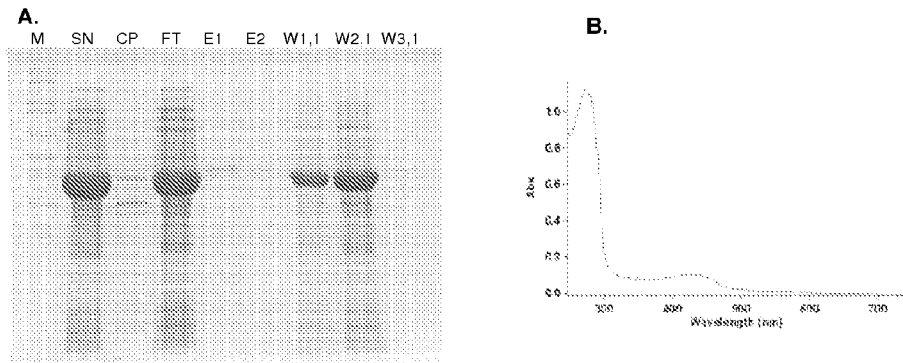
FIG. 4 shows SDS-PAGE and UV-VIS data on purified samples of EgtE; 4A shows SDS-PAGE data for a molecular weight marker (lane M), supernatant (lane SN), cell pellet (lane CP), flow through (lane FT), elution fractions 1 and 2 (lanes E1 and E2, respectively), and wash fractions 1, 2, and 3 (lanes W1,1, W2,1, and W3,1, respectively); 4B shows UV-VIS data on purified EgtE that is consistent with the presence of a PLP cofactor.

Improving the Activities of Mono-nuclear Non-heme Iron Enzymes. Seebeck confirmed EgtA, EgtB, EgtC, and EgtD functions by demonstrating activities in vitro. However, despites extensive efforts from them on examining various ways for EgtE production, EgtE protein cannot been overexpressed or purified.[9] Thus, ergothioneine production thorough synthetic biology is not possible. In our preliminary studies, we have successfully overexpressed and purified EgtE (FIG. 4A). The UV-visible spectrum of purified EgtE is shown in FIG. 4B and the absorption feature at around 400 nm is consistent with the presence of a PLP cofactor. One of the most important discoveries from these efforts is that EgtE may need to be co-expressed with another gene, e.g., called FAD-synthetase.

Optimize ergothioneine production biosynthetic pathway. In the above section, we have successfully solved the EgtE problems, which enable ergothioneine production through metabolic engineering. However, the original ergothioneine biosynthetic pathway (FIG. 1A) is not efficient. To solve this problem, we initiated the search for enzymes that can oxidatively couples hercynine (2) and Cys directly as outlined in FIG. 2. Two of such enzymes (OvoA in FIG. 1B and NcEgt-1 from *Neurospora crassa*[13]) have been identified by a combination of bioinformatics analysis and activity analysis using oxygen and $^1$H-NMR assays.

According to the initial reports from Seebeck,[9-10] EgtB and OvoA distinguish themselves from each other by both their substrate preferences and their product C—S bond regio-selectivity (FIG. 1). The C—S bond in ergothioneine (5) is located at the histidine ε-carbon, while for ovothiol, the C—S bond is located at the histidine δ-carbon (8). Their substrate preferences are also different. EgtB catalyzes the oxidative coupling between hercynine (2) and γ-Glu-Cys. OvoA preferentially couples His and Cys (FIG. 1B). As a first step toward achieving the goal outlined in FIG. 2, we examined EgtB activity using hercynine (2) and Cys as substrates. As initially reported by Seebeck, EgtB cannot recognize Cys as the substrate. Thus, it is not possible to achieve the direct coupling between hercynine (2) and Cys using EgtB as the catalyst. Such a desired enzyme can be obtained by either directed evolution of EgtB to alter its substrate specificity or by searching for enzymes that have preference for Cys. One of such enzyme identified is OvoA. The proposed biological activity of OvoA is the oxidative coupling of His and Cys and indeed, OvoA has this proposed activity (FIG. 1B). Surprising, when hercynine (2) was used to replace His as a substrate, we found that OvoA can also make use of hercynine (2) as a substrate. Kinetic analysis of OvoA in air-saturated HEPES buffer revealed the following kinetic parameters for the oxidative coupling between Cys and hercynine 2): $k_{cat}$ of 270±5 min$^{-1}$ and a $K_m$ of 395±30 μM for hercynine, a $K_m$ of 3.19±0.41 mM for Cys. The $k_{cat}$ is only two-fold less than that of the reaction using His as the substrate.

Figure 5:
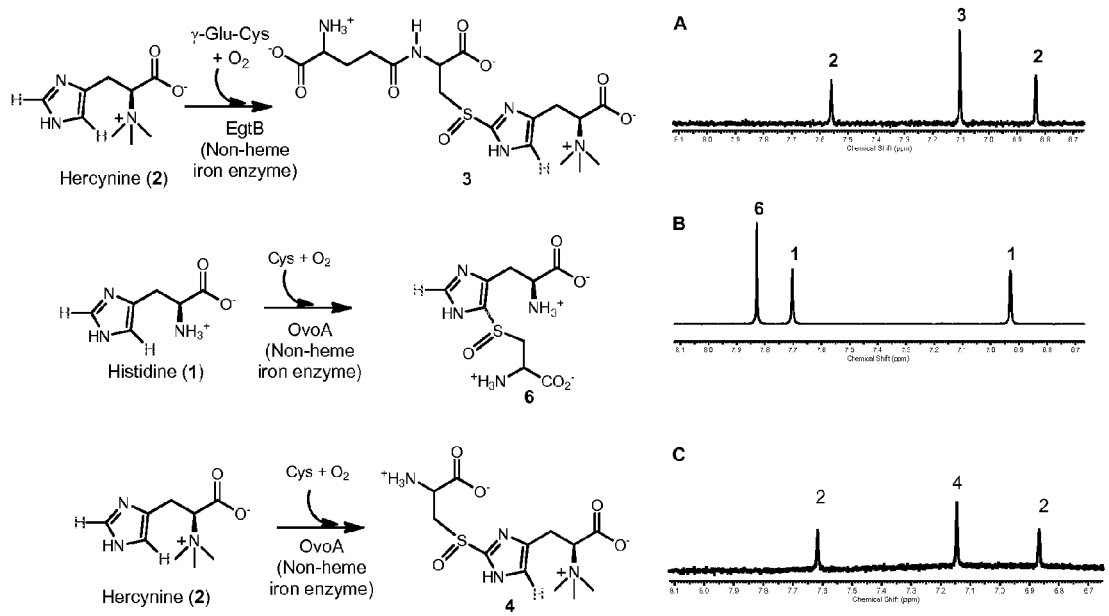
FIG. 5 shows (A) EgtB catalyzed conversion of 2 to 3 with corresponding NMR data, (B) OvoA catalyzed conversion of 1 to 6 with corresponding NMR data, and (C) OvoA catalyzed conversion of 2 to 4 with corresponding NMR data.

More importantly, when the product was analyzed by $^1$H-NMR assay, the product is compound 4(FIG. 5C) instead of a compound with the C—S linkage of its native OvoA reaction (FIG. 1B and FIG. 5A). In $^1$H-NMR spectrum of the OvoA-catalyzed coupling reaction between hercynine (2) and Cys, a new signal is seen at 7.45 ppm. According to the information discussed in FIG. 3, this signal most likely comes from the imidazole H-atom of an EgtB-type of coupling product, which implies that Cys and hercynine (2) are oxidatively coupled at the histidine ε-carbon instead of the δ-carbon, which led to our initial assignment of 4as the OvoA-catalyzed oxidative coupling product between Cys and hercynine (FIG. 5C). To provide definitive answers, the oxidative coupling product between hercynine (2) and Cys was isolated and characterized by mass spectrometry and several NMR-spectroscopies ($^1$H-NMR, $^{13}$C-NMR, and 2D-NMR including COSY, HMBC and HMQC, supporting information in 1$^{st}$ manuscript). All of these data provide strong evidence supporting an OvoA-catalyzed production of 4 from a direct oxidative coupling of hercynine (2) and Cys, which allow us to achieve the goal outlined in FIG. 2, the one-step 2→4 conversion.

Based on this exciting discovery, we have also examined another protein NcEgt-1 from *Neurospora crassa*[13]. Indeed, NcEgt-1 can also catalyze the oxidative coupling of hercynine (2) and Cys to form 4 with an activity on the same order of magnitude as OvoA catalyzed 2→4 conversion.

In summary, in our studies, we have overcome all of the three challenges to produce ergothioneine production through metabolic engineering: 1) Identifying the factors governing the metallo-enzyme activities (OvoA, EgtB metallo-cofactor installation and preventing enzyme inactivations); 2) Successful direct 2→4 conversion to simplify the biosynthetic pathway and eliminating the competition between ergothioneine and glutathione biosynthesis; 3) Figuring out conditions to overexpress EgtE protein. With these achievements, we have successfully established two different ergothioneine biosynthetic pathway outlined in FIG. 2: 1) the production of ergothioneine by the original ergothioneine pathway (FIG. 2A) after the successful production of EgtE; 2) the production of ergothioneine through a shorter pathway (FIG. 2B) after the discovery of enzymes capable of direct 2→4 conversion and the successful production of EgtE. In the subsequent section, we will describe in vivo ergothioneine production through fermentation.

Ergothioneine Production Through Metabolic Engineering.

Figure 6:
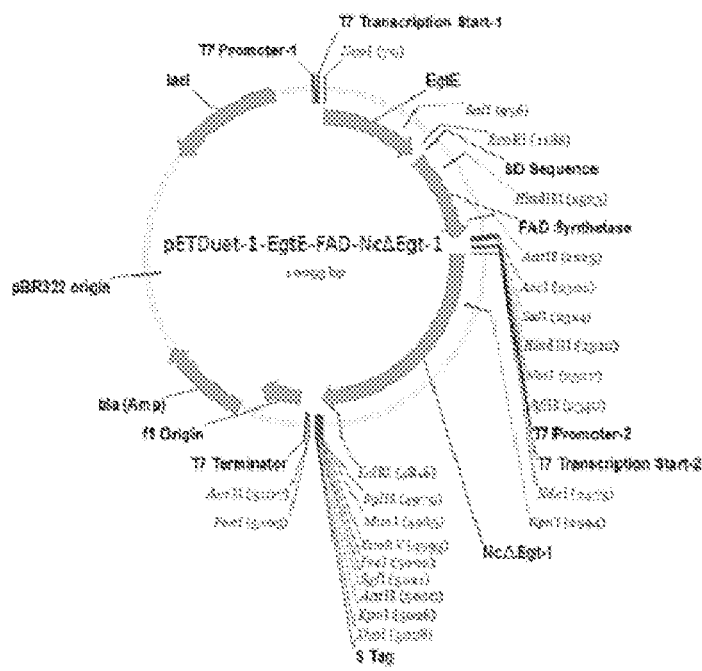
FIG. 6 is a schematic representation of an expression vector (construct Ego-1) for the production of ergothioneine in a cell, e.g. an E. coli cell.
Figure 7:
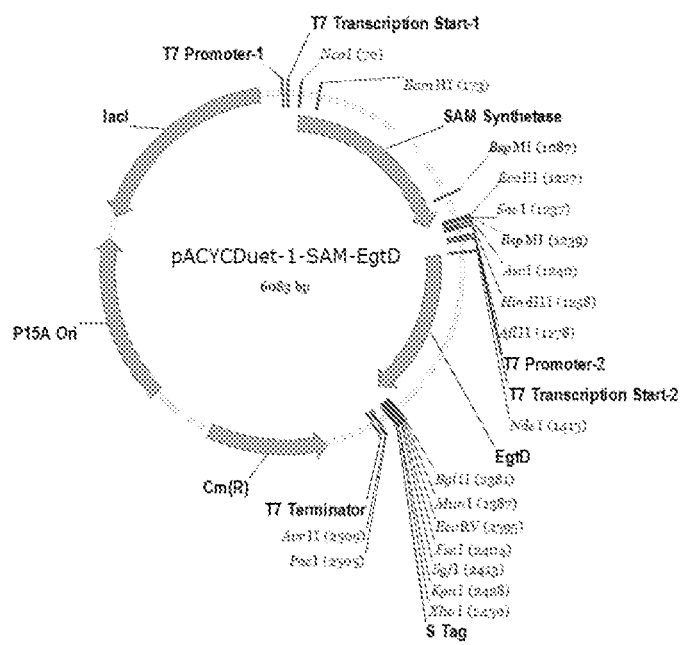
FIG. 7 is a schematic representation of an expression vector (construct Ego-2) for further enhancing the production of ergothioneine.
Figure 8:
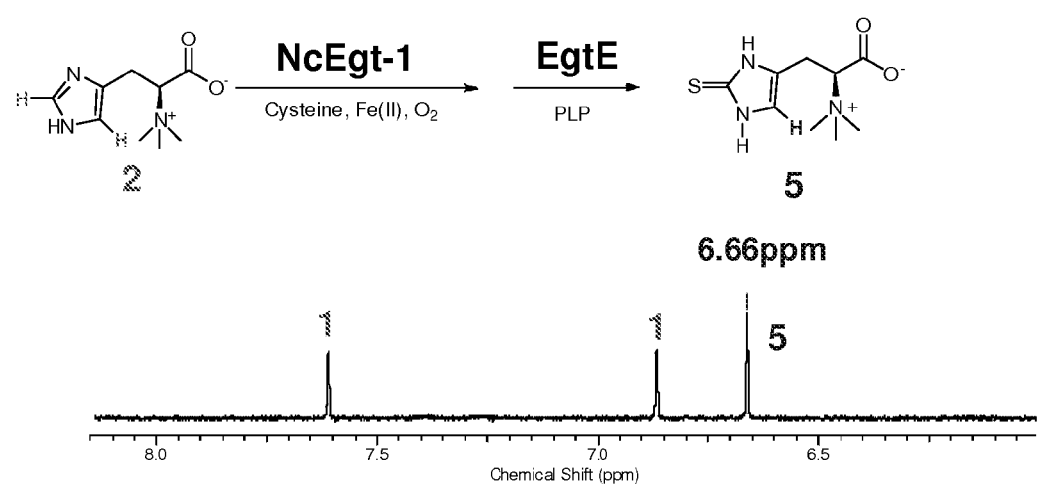
FIG. 8 shows the conversion of hercynine to ergothioneine catalyzed by NcEgt1 and EgtE.
Figure 9:
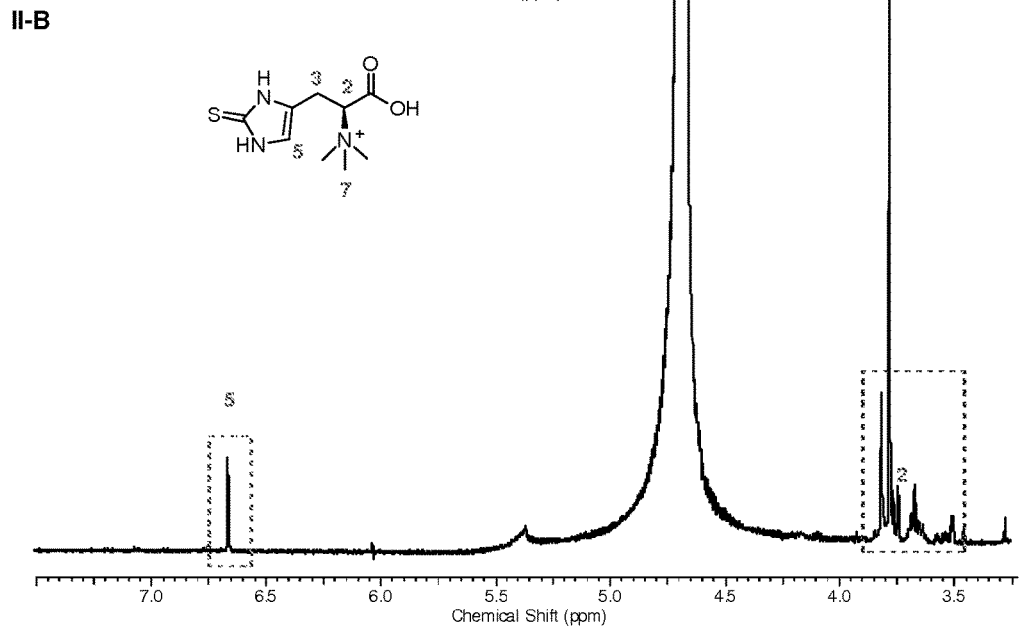
FIGS. 9A and 9B show the $^1$H-NMR spectra of partially purified ergothioneine from E. coli cells transformed with both Ego-1 and Ego-2 vectors described in FIGS. 6 and 7 and pure ergothioneine.

Method I: According to the new ergothioneine biosynthetic pathway outlined in FIG. 2, only two steps are needed: the oxidative coupling between hercynine (2) and Cys to compound 4 catalyzed by OvoA or NcEgt-1(2→4 conversion) and EgtE-catalyzed C—S lysis step (4→5 conversion, FIG. 2). Because EgtE production is achievable only if when EgtE is co-expressed with another gene (e.g., a FAD synthetase gene), thus, a minimal ergothioneine biosynthetic gene cluster can be assembled using three genes (OvoA or NcΔEgt-1, EgtE, and FAD synthetase). We have cloned EgtE and FAD into a multiple cloning site I of pETDuet vector and NcEgt-1 gene into the multiple cloning site II to create a construct and named it as (Ego-1) as shown in FIG. 6.

To produce ergothioneine using Ego-1 vector, it can be transformed into *E. coli* BL(21) DE3 cell is transformed with Ego-1 vector and the desired cell is selected on LB plates supplemented with 100 μg/mL of Amp. To produce ergothioneine, overnight culture of the above cell are be used to inoculate fresh LB or TB medium (supplemented with 100 μg/mL of Amp., 1 mM of hercynine, 1 mM of Cys and 1 mM of Met) at 37° C. When $OD_{600}$ reaches 0.6, the temperature of the culture medium is reduced to 25° C. and ergothioneine production is initiated by adding 0.4-1 mM of IPTG to induce NcEgt-1, EgtE, and FAD synthetase production. Ergothioneine production can be monitored by withdrawing 1 mL of culture medium and directly analyzing the hercynine concentration overtime by $^1$H-NMR. Once all hercynine are consumed or the production of ergothioneine stops to further increase, the fermentation process is stopped. Supernatant and cells are separated by centrifugation. Ergothioneine from both supernatant and the cell pellet were isolated using ion-exchange chromatography.

Method II: Using method I, we need to supplement the culture medium with hercynine (2), which has been chemically synthesized in our laboratory. To further reduce the fermentation cost, we created a second plasmid (Ego-2) by cloning EgtD gene into multiple cloning site II in pACYC-Duet vector and SAM synthetase gene into multiple cloning site I. With the introduction of EgtD gene, which is responsible for the methylation of histidine to hercynine (2), we can supplement the culture medium with His instead of hercynine (2), which will further reduce the fermentation cost. Because this methylation process needs another co-substrate, S-adenosylmethioneine (SAM), the introducing of SAM synthetase will ensure the maximal activity of EgtD in His→Hercynine (2) conversion. Because SAM synthetase substrates are methionine and ATP, besides His, Met will be included as another medium supplement.

To produce ergothioneine under optimal condition, BL21 (DE3) *E. coli* cells are transformed with both Ego-1 and Ego-2 and selected on LB plates supplemented with 100 μg/mL of Amp and 20 μg/mL of chlorophenicol. The BL21 (DE3)-Ego1-Ego2 overnight culture is then used to inoculate fresh LB or TB medium supplemented with 100 μg/mL of Amp and 20 μg/mL of chlorophenicol, 1 mM of His, 1 mM of Met at 37° C. When $OD_{600}$ reaches 0.6, the temperature is reduced to 25° C. and ergothioneine production will be induced with 0.4-1 mM IPTG. Ergothioneine production can be monitored by withdrawing 1 mL of culture medium and directly analyzing the His concentration overtime by $^1$H-NMR. Once all His are consumed or the production of ergothioneine stops to further increase, the fermentation process will be stopped. Supernatant and cells are separated by centrifugation. Ergothioneine from both supernatant and the cell pellet were isolated using ion-exchange chromatography.

In one cell-free enzymatic transformation synthesis of ergothioneine, the reaction mixture contained OvoA, EgtE, hercynine and cysteine in a TCEP buffer. The reaction was conducted at 25° C. under aerobic conditions. The reaction was monitored by $^1$H-NMR and once the reaction was complete, ergothioneine was purified using ion-exchange chromatography.

REFERENCES

1. Tanret, C., Comptes rendus de l'Académie des Sciences, 1909. 149: p. 222-224.
2. Grundemann, D., et al., *Discovery of the ergothioneine transporter*. Proceedings of the National Academy of Sciences of the United States of America, 2005. 102(14): p. 5256-61.
3. Melville, D. B. and S. Eich, *The occurrence of ergothioneine in plant material*. Journal of Biological Chemistry, 1956. 218(2): p. 647-51.
4. Fahey, R. C., et al., *Analysis of biological thiols: quantitative determination of thiols at the picomole level based upon derivatization with monobromobimanes and separation by cation-exchange chromatography*. Analytical Biochemistry, 1981. 111(2): p. 357-65.
5. Genghof, D. S., et al., *Ergothioneine in microorganisms*. Journal of Biological Chemistry, 1956. 223(1): p. 9-17.
6. Briggs, I., *Ergothioneine in the central nervous system*. Journal of Neurochemistry, 1972. 19(1): p. 27-35.
7. Epand, R. M., R. F. Epand, and S. C. Wong, *Study of the ergothioneine concentration in the blood of individuals with diabetes mellitus*. Journal of Clinical Chemistry & Clinical Biochemistry, 1988. 26(10): p. 623-6.

8. Hartman, P. E., *Ergothioneine as antioxidant*. Methods in Enzymology, 1990. 186: p. 310-8.
9. Hand, C. E. and J. F. Honek, *Biological chemistry of naturally occurring thiols of microbial and marine origin*. Journal of Natural Products, 2005. 68(2): p. 293-308.
10. Fahey, R. C., *Novel thiols of prokaryotes*. Annual Review of Microbiology, 2001. 55: p. 333-56.
11. Weaver, K. H. and D. L. Rabenstein, *Thiol-Disulfide Exchange-Reactions of Ovothiol-a with Glutathione*. Journal of Organic Chemistry, 1995. 60(6): p. 1904-1907.
12. Scott, E. M., I. W. Duncan, and V. Ekstrand, *Purification and Properties of Glutathione Reductase of Human Erythrocytes*. Journal of Biological Chemistry, 1963. 238: p. 3928-33.
13. Paul, B. D. and S. H. Snyder, *The unusual amino acid L-ergothioneine is a physiologic cytoprotectant*. Cell Death & Differentiation, 2010. 17(7): p. 1134-40.
14. Seebeck, F. P., *In vitro reconstitution of Mycobacterial ergothioneine biosynthesis*. Journal of the American Chemical Society, 2010. 132(19): p. 6632-3.
15. Chiang, P. K., et al., *S-adenosylmethionine and methylation*. FASEB Journal, 1996. 10(4): p. 471-480.
16. Braunshausen, A. and F. P. Seebeck, *Identification and characterization of the first ovothiol biosynthetic enzyme*. Journal of the American Chemical Society, 2011. 133(6): p. 1757-9.
17. Xu, J. Z. and J. C. Yadan, *Synthesis of L-(+)-Ergothioneine*. Journal of Organic Chemistry, 1995. 60(20): p. 6296-6301.
18. Erdelmeier, I., et al., *Cysteine as a sustainable sulfur reagent for the protecting-group-free synthesis of sulfur-containing amino acids: biomimetic synthesis of L-ergothioneine in water*. Green Chemistry, 2012. 14, p. 2256-2265.
19. Baldwin, J. E. and M. Bradley, *Isopenicillin-N Synthase-Mechanistic Studies*. Chemical Reviews, 1990. 90(7): p. 1079-1088.
20. Bello, M. H., et al., *The Neurospora crassa mutant Nc Delta Egt-1 identifies an ergothioneine biosynthetic gene and demonstrates that ergothioneine enhances conidial survival and protects against peroxide toxicity during conidial germination*. Fungal Genetics and Biology, 2012. 49(2): p. 160-172.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A process for preparing ergothioneine, the process comprising:
   (i) incubating histidine or hercynine with a reaction mixture comprising recombinantly expressed:
      (a) EgtA protein,
      (b) EgtB protein,
      (c) EgtC protein,
      (d) EgtD protein, and
      (e) EgtE protein, wherein the EgtE protein is produced from recombinant coexpression with a gene encoding a FAD synthetase to facilitate EgtE production; and
   (ii) isolating ergothioneine from the reaction mixture.

2. A process for preparing ergothioneine, the process comprising:
   (i) incubating hercynine with a reaction mixture comprising recombinantly expressed:
      (a) OvoA protein and
      (b) EgtE protein; and
   (ii) isolating ergothioneine from the reaction mixture.

3. A process of claim 2, wherein the reaction mixture further comprises recombinantly expressed EgtD protein.

4. The process of claim 1, wherein the EgtD protein is recombinantly co-expressed with a gene encoding SAM synthetase.

5. The process of claim 1, wherein the enzymatic mixture further comprises methionine or cysteine.

6. The process of claim 1, wherein the enzymatic mixture further comprises an iron salt.

7. The process of claim 1, wherein the reaction mixture comprises a cell lysate.

8. A process for preparing ergothioneine, the process comprising:
   (i) incubating hercynine with a reaction mixture comprising recombinantly expressed:
      (a) NcEgt1 protein and
      (b) EgtE protein, wherein the EgtE protein is produced from recombinant coexpression with a gene encoding a FAD synthetase to facilitate EgtE production; and
   (ii) isolating ergothioneine from the reaction mixture.

9. A process of claim 8, wherein the reaction mixture further comprises recombinantly expressed EgtD protein.

* * * * *

SEQUENCE LISTING

<160> NUMBER OF SEQ ID NOS: 6

<210> SEQ ID NO 1
<211> LENGTH: 2160
<212> TYPE: DNA
<213> ORGANISM: Erwinia tasmaniensis

<400> SEQUENCE: 1

```
atggcaaaat gggagcacga cgtgaccgcg caacaacacc agacaggatt acccgcccca        60 accegcatge tgacgctcag cggtggcgat ccacaacaaa aacgactgca gatactgagc       120
gacttcagca agacctggga actctatgaa agcctgtttg actgccttac cgatgagcgc       180
gcctggtaca ccaaggccat ttcactgcgt cacccgctga tcttctatta cggccatacc       240
gccaccttct atatcaacaa gttgatggcg gggggcctta tcgacgcgcg cgttgacgac       300
aggatcgaag cgacaatggc gattggcgtc gacgaaatga gctgggacga cctggataac       360
agccactaca gctggccgtc gctggcagaa ctgcgcgact atcgtggaaa agttcgccac       420
ctcgttgagc agtttattca gcagatgccg ttgacgttgc cgatcggctg ggatagcccg       480
gcatgggtta tcctgatggg gatcgagcat gagcgcatcc atctggaaac ctcaagcgtg       540
ctgatccgcc agctgccgct ggcgtgggtc agcgcccagc cgcactggcc tgcctgtccc       600
gatgcgcgtc acgatcgtat ggcggtgccg gccaacagcc tggtacaggt cgccggtcgc       660
cgcgtgacgc aggggaaaac ggatgatacc tacggctggg ataatgagta cggcagcctg       720
gtcaccgaag tgaagccatt tcaggccagc cgcatgctgg tcagtcatgc cgaattttt        780
```

```
gctttcgttg ccgcgggagg ctatcagaac caacgctggt gggatgacga aggctggggc    840
tggcgtgaat tttccgcggc ggagatgccg acctttggc gaggttcacc acagcagccg      900
gaagaattaa ggctgcgcct gctggcagaa gaagtggcga tgccgtggga ctggccggcc    960
gaggtcaatc agctggaggc tgccgcattc tgccgctgga aagcggagga gaccggcctg    1020
tcgatccagc tgccggcgga gagtgaatgg atgagcctgc gcgagcaggt tgagggcgac    1080
cagccggact ggaatgatgc accgggcaat attaatctgg cctgctgggc atcttcttgc    1140
ccaatagacc gctttgccca gggcgaattc ttcgacctgg ttggcaatgt ctggcagtgg    1200
accacgacgc caatcaacgg ttttccgggc tttcgcgtcc accctttata cgatgatttc    1260
tccaccccga cctttgatgg caaacacacg ctgattaagg gcggcagctg gatatctacc    1320
ggcaatgagg ccctgaaatc tgctcgctat gccttccgac gccatttctt ccagcatgcg    1380
ggattccgct atgtggtttc gcaacatcag gagagcctgc actccaaccc gtatgaaacg    1440
gacagcatgg tgtcacagta tctcgatttc cagtacggcc agagtactt cgccgtggaa    1500 aattacgcca aggcgctggc gaagatcgcc tgcggtatca gtcagcacca ccagcgcgcg    1560
ctggatatcg gctgtgctac cggacgtgcc agctttgagc tggcgcgtca ttttgagcag    1620
gtggtcggaa tggactactc ggcgcgtttt atcgacgtgg ctctgcaact gacccgcggc    1680
gaagatttcc gctatgtcac ccaggaagaa ggcgacctgg tcgaataccg tcaggtgcat    1740
ttgccggact cgatctcgg cccggagcag gccagccgca tccggtttgt acaggggggat    1800 gcctgcaacc tgaaacccca gcaggaagcc tgggatctgg tgctggccgc taacctgatt    1860
gaccgcctgc gccagccggc gcgcttcctt gcggacatcg cgcccatgat ccgcccggc    1920 ggcgtactga tgctctcatc cccctatact tggcttgaag agttcacgcc gaaagagaac    1980
tggctgggcg gcattcgtga aaacggcgaa gcgctctcga cttatcaggc gctgcaacgt    2040
ctgctggccg ccgactttga ggagctggcc ccgcctcagg acgtgccgtt tgtcattcgt    2100
gaaacggcgc gcaaatatca gcacagcgtg gcgcagttaa ccctgtggcg taaacgttag    2160
```

<210> SEQ ID NO 2
<211> LENGTH: 2502
<212> TYPE: DNA
<213> ORGANISM: Neurospora crassa OR74A

<400> SEQUENCE: 2

```
atgccgagtg ccgaatccat gaccccaagc agtgccctcg gacagctcaa agcaactgga    60
caacatgtgc tatccaagct tcagcagcag acatcaaacg ccgatatcat cgacatccgc    120
cgcgttgctg tagagatcaa cctcaagacc gagataacct ccatgttccg acctaaagat    180
ggccctagac agctacccac cttgcttctc tacaacgaga gaggcctgca gctgttcgag    240
cgtatcacat accttgaaga gtactatctt accaatgacg agatcaaaat cctcaccaaa    300
catgcgaccg aaatggctag cttcatcccg tcaggtgcca tgatcattga gctcggaagc    360
ggaaatctgc gcaaagtaaa ccttctattg gaagccctag acaacgccgg caaggcaatt    420
gactattatg cccttgacct gtctcgggag gagctggagc gcactctcgc tcaggtacca    480
tcctacaagc acgtcaagtg ccacggtctt ctgggtacat atgacgatgg acgtgactgg    540
ctcaaggccc cagagaacat caataaacag aaatgcatct tgcacctcgg gtcaagcatt    600
gacaaggttg gtattactca cgagttcatc ttgaatggtc ttcgcaacgc caatgaaatt    660
atcggagaga cggccttcat cgagggcgat tggagagtca ttggcgaata tgtgtatgac    720
gaagagggcg gcagacacca ggccttttac gccccactc gcgacaccat ggttatgggg    780
```

```
gagttgatta ggtcacacga caggatccag atcgaacaga gcctaaagta ctcgaaagag    840
gagtcagaga ggctctggag cacggcggga ttggaacaag tctcggaatg gacgtacggc    900
aacgaatatg gactccatct gcttgccaag tcaaggatgt ctttcagtct catcccttcg    960
gtgtacgctc gcagcgcact cccaactctg gacgactggg aggcccttg ggcgacatgg    1020 gatgtcgtca cacgtcagat gcttccccag gaagagcttc tggagaagcc catcaagctc    1080
cgaaacgcct gcatctttta cctcggtcac atcccgacct tcctcgacat ccagctcaca    1140
aagaccacca agcaggctcc gtcagagccc gctcactttt gcaagatctt cgagcgaggc    1200
attgatcctg atgtcgacaa cccggagctg tgtcatgcgc actcggagat tcctgatgaa    1260
tggccgccgg tggaagaaat cctgacctac caggagacgg tacggtcccg gttacgcggc    1320
ctctatgcgc atggcatcgc gaatattccg cggaatgtgg gtcgggccat ttgggttggg    1380
tttgagcacg agcttatgca tatcgagacg ctgttgtaca tgatgctaca gagcgacaag    1440
acgctgatcc aacccatat tccacggccc gactttgaca agctcgcgag gaaggcagag    1500
tccgagaggg ttcccaatca gtggtttaag attccggcac aggagatcac catcggtttg    1560
gatgatcctg aggatggatc tgatatcaac aagcattatg gctgggacaa cgagaagcct    1620
ccaaggcgcg ttcaagttgc tgcctttcag gctcaaggga ggccgatcac caacgaagag    1680
tacgcgcaat atctgcttga aaagaacatc gacaagctcc ctgcctcttg ggcccgcctg    1740
gacaacgaga acattagcaa tggaacaaca acagcgtga gcggtcacca cagcaacaga    1800
acctccaagc agcagctccc ttcatctttc ctcgagaaga cagcagtccg cacagtctac    1860
ggtctcgtgc ctctcaagca cgctctcgac tggcccgtgt ttgcctctta cgacgaactt    1920
gccggttgcg cagcttacat gggcggccgt attcccacct tcgaagagac ccggagcatt    1980
tacgcttacg ccgatgctct caagaagaag aaggaagctg agagacaatt gggaaggacg    2040
gttccggctg ttaatgccca cctaaccaac acggcgtgg aaatcactcc cccatcctct    2100
ccctcttccg agaccccgc cgagtcttcc tccccctccg acagcaacac caccctcatc    2160
accaccgaag acctcttctc tgacctagac ggtgccaatg tcggtttca caactggcac    2220 cctatgccca tcacctccaa aggcaacacc cttgtcgggc aaggcgagct cggcggcgtg    2280
tgggaatgga cttcatcggt cctccgcaag tgggaggggt tcgagccgat ggagctgtac    2340
cccggctata cggcggattt tttcgatgag aagcacaaca ttgtgctggg agggagctgg    2400
gctacgcatc cgaggattgc ggggaggaag agctttgtga attggtacca gaggaattat    2460
ccttatgctt gggtgggggc gagagttgtt agggatttgt ga                      2502
```

<210> SEQ ID NO 3  
<211> LENGTH: 966  
<212> TYPE: DNA  
<213> ORGANISM: Mycobacterium smegmatis str. MC2 155

<400> SEQUENCE: 3

```
atgacgctct cactggccaa ctacctggca gccgactcgg ccgccgaagc actgcgccgt    60
gacgtccgcg cgggcctcac cgcggcaccg aagagtctgc cgcccaagtg gttctacgac    120
gccgtcggca gtgatctgtt cgaccagatc acccggctcc ccgagtatta ccccacccgc    180
accgaggcgc agatcctgcg gacccggtcg gcggagatca tcgcggccgc gggtgccgac    240
accctggtgg aactgggcag tggtacgtcg gagaaaaccc gcatgctgct cgacgccatg    300
cgcgacgccg agttgctgcg ccgcttcatc ccgttcgacg tcgacgcggg cgtgctgcgc    360
```

```
tcggccgggg cggcaatcgg cgcggagtac cccggtatcg agatcgacgc ggtatgtggc    420
gatttcgagg aacatctggg caagatcccg catgtcggac ggcggctcgt ggtgttcctg    480
gggtcgacca tcggcaacct gacacccgcg ccccgcgcgg agttcctcag tactctcgcg    540
gacacgctgc agccgggcga cagcctgctg ctgggcaccg atctggtgaa ggacaccggc    600
cggttggtgc gcgcgtacga cgacgcggcc ggcgtcaccg cggcgttcaa ccgcaacgtg    660
ctggccgtgg tgaaccgcga actgtccgcc gatttcgacc tcgacgcgtt cgagcatgtc    720
gcgaagtgga actccgacga ggaacgcatc gagatgtggt tgcgtgcccg caccgcacag    780
catgtccgcg tcgcggcact ggacctggag gtcgacttcg ccgcgggtga ggagatgctc    840
accgaggtgt cctgcaagtt ccgtcccgag aacgtcgtcg ccgagctggc ggaagccggt    900
ctgcggcaga cgcattggtg gaccgatccg gccggggatt tcgggttgtc gctggcggtg    960
cggtga                                                               966
```

<210> SEQ ID NO 4
<211> LENGTH: 1116
<212> TYPE: DNA
<213> ORGANISM: Mycobacterium smegmatis str. MC2 155

<400> SEQUENCE: 4

```
gtgatgctcg cgcagcagtg gcgtgacgcc cgtcccaagg ttgccgggtt gcacctggac     60
agcggggcat gttcgcggca gagcttcgcg gtgatcgacg cgaccaccgc acacgcacgc    120
cacgaggccg aggtgggtgg ttatgtggcg gccgaggctg cgacgccggc gctcgacgcc    180
gggcgggccg cggtcgcgtc gctcatcggt tttgcggcgt cggacgtggt gtacaccagc    240
ggatccaacc acgccatcga cctgttgctg tcgagctggc cggggaagcg cacgctggcc    300
tgcctgcccg cgagtacggg ccgaatctg tctgccatgg cggccaacgg tttccaggtg    360
cgtgcgctac cggtcgacga cgacgggcgg gtgctggtcg acgaggcgtc gcacgaactg    420
tcggcccatc ccgtcgcgct cgtacacctc accgcattgg caagccatcg cgggatcgcg    480
caacccgcgg cagaactcgt cgaggcctgc cacaatgcgg ggatcccgt ggtgatcgac     540 gccgcgcagg cgctggggca tctggactgc aatgtcgggg ccgacgcggt gtactcatcg    600
tcgcgcaagt ggctcgccgg cccgcgtggt gtcggggtgc tcgcggtgcg gcccgaactc    660
gccgagcgtc tgcaaccgcg gatcccccg tccgactggc caattccgat gagcgtcttg     720
gagaagctcg aactaggtga gcacaacgcg gcggcgcgtg tgggattctc cgtcgcggtt    780
ggtgagcatc tcgcagcagg gcccacgcgc gtgcgcgaac gactcgccga ggtggggcgt    840
ctctctcggc aggtgctggc agaggtcgac gggtggcgcg tcgtcgaacc cgtcgaccaa    900
cccaccgcga tcaccaccct tgagtccacc gatggtgccg atcccgcgtc ggtgcgctcg    960
tggctgatcg cggagcgtgg catcgtgacc accgcgtgtg aactcgcgcg ggcaccgttc   1020
gagatgcgca cgccggtgct gcgaatctcg ccgcacgtcg acgtgacggt cgacgaactg   1080
gagcagttcg ccgcagcgtt gcgtgaggcg ccctga                             1116
```

<210> SEQ ID NO 5
<211> LENGTH: 1017
<212> TYPE: DNA
<213> ORGANISM: Corynebacterium stationis

<400> SEQUENCE: 5

```
gtggatattt ggtacggaac agcagcagtc ccaaaagact tagacaacag tgcagtcacc     60
attggtgtct tcgacggcgt gcatcgcggg catcagaaat tgattaatgc cactgttgaa    120
```

```
aaagcacgcg aggtgggcgc gaaagccatc atggttactt ttgacccgca cccagtgtcc      180
gtgtttctcc cgcgccgtgc gccgctgggg attactacct tggctgagcg ctttgcgctg      240
gcggaaagct ttggcattga tggcgtgcta gtcattgatt ttacccgcga actctctggt      300
acttcgccgg agaagtacgt ggaatttctt ctagaagaca cgctgcatgc ctcacacgtg      360
gtggtcggag ctaactttac ttttggggaa aatgccgccg gcaccgcaga ttccttgcgg      420
cagatttgcc agtcgcgttt gaccgttgat gtcatcgact tgcttgacga tgaaggcgtg      480
aggatctctt ccacgaccgt gcgcgagttt ctatctgaag agatgttgc gcgagccaac       540 tgggctttgg ggcggcactt ttatgtcaca ggtccagtag tccgtggtgc tggccgcgga      600
ggcaaggagc tgggatttcc cacggcgaat cagtactttc acgatactgt cgctttgcct      660
gccgatgggg tctatgccgg ctggttgacc attttgccca ccgaggcacc cgtaagcggg      720
aatatggaac ctgaggtggc ttatgccgcc gctatttcag tgggaaccaa cccgaccttt      780
ggcgatgagc agcgttctgt ggagtctttt gtactcgata gagatgctga tctttatggt      840
cacgacgtca agtggaatt tgttgaccac gtgcgggcaa tggaaaagtt tgactccgtc       900
gagcagcttt tggaagtcat ggctaaagac gtgcagaaaa cccgcacttt gctagctcag      960
gatgtgcaag cacataagat ggcgcctgag acctactttc tacaagcaga aagctaa       1017

<210> SEQ ID NO 6
<211> LENGTH: 1155
<212> TYPE: DNA
<213> ORGANISM: Escherichia coli

<400> SEQUENCE: 6
atggcaaaac acctttttac gtccgagtcc gtctctgagg gccatcctga caaaattgct       60
gaccaaattt ctgatgccgt tttagacgcg atcctcgaac aggatccgaa agcacgcgtt      120
gcttgcgaaa cctacgtaaa aaccggcatt ggttttagtt ggcggcgaaa tcaccaccag      180
cgaccttggg tagacatcga agagatcacc cgtaacaccg ttcgcgaaat tggctatgtg      240
cattccgaca tgggctttga cgctaactcc tgtgcggttc tgagcgctat cggcaaacag      300
tctcctgaca tcaaccaggg cgttgaccgt gccgatccgc tggaacaggg cgcgggtgac      360
cagggtcttg atgtttcggc tacgcaacta atgaaaccga cgtgcctgat gccagcacct      420
atcacctatg cccaccgtct ggtacagcgt caggctgaag tgcgtaaaaa cggcactctg      480
cgtgtgcgcc cggacgcgaa aagccaggtg acttttagct atgacgacgg caaaatcgtt      540
ggtatcgatg ctgtcgtgct ttccactcag cactctgaag agatcgacca gaaatcgctg      600
caagaagcgg taatggaaga gatcatcaag ccaattctgc ccgctgaatg gctgacttct      660
gccaccaaat tcttcatcaa cccgaccggt cgtttcgtta tcggtggccc aatgggtgac      720
tgcggtctta ctggtcgtaa aattatcgtt gatactaccg gcggcatggc gcgtcacggt      780
ggcggtgcat tctctggtaa agatccatca aaagtggacc gttccgcagc ctacgcagca      840
cgttatgtcg cgaaaaacat cgttgctgct ggcctggccg atcgttgtga aattcaggtt      900
tcctacgcaa tcggcctggc tgaaccgacc tccatcatgg tagaaacttt cggtactgag      960
aaagtgcctt ctgaacaact gacccctgctg gtacgtgagt tcttcgacct gccaatcggt     1020
ctgattcaga tgctggatct gctgcacccg atctacaaag aaaccgcagc atacggtcac     1080
tttggtcgtg aacatttccc gtgggaaaaa accgacaaag cgcagctgct gcgcgatgct     1140
gccggtctga agtaa                                                       1155
```